US 8,008,268 B2

(12) United States Patent
Yao et al.

(10) Patent No.: US 8,008,268 B2
(45) Date of Patent: Aug. 30, 2011

(54) VACCINES AGAINST VESICULAR STOMATITIS

(75) Inventors: Jiansheng Yao, North York (CA); Jules Maarten Minke, Corbas (FR); Jean Christophe Audonnet, Lyons (FR)

(73) Assignee: Merial Limited, Duluth, GA (US)

( * ) Notice: Subject to any disclaimer, the term of this patent is extended or adjusted under 35 U.S.C. 154(b) by 687 days.

(21) Appl. No.: 11/505,064

(22) Filed: Aug. 16, 2006

(65) Prior Publication Data

US 2008/0124357 A1      May 29, 2008

Related U.S. Application Data

(60) Provisional application No. 60/833,208, filed on Jul. 25, 2006.

(51) Int. Cl.
*C07H 21/02* (2006.01)
*C12N 15/33* (2006.01)
*C12N 15/39* (2006.01)
*A61K 48/00* (2006.01)
*C12N 15/47* (2006.01)

(52) U.S. Cl. ................. 514/44 R; 435/320.1; 536/23.72

(58) Field of Classification Search ........................ None
See application file for complete search history.

(56) References Cited

U.S. PATENT DOCUMENTS

| 6,541,458 | B1 | 4/2003 | Audonnet et al. |
| 6,969,598 | B2 | 11/2005 | Olsen et al. |
| 2006/0160220 | A1 | 7/2006 | Bremel et al. |

OTHER PUBLICATIONS

Facciabene et al. Journal of Virology, Aug. 2004, vol. 78, No. 16, pp. 8663-8672.*
Flanagan et al. (Journal of Virology, Sep. 2000, vol. 74, No. 17, pp. 7895-7902.*
Wright et al. The Journal of Infectious Diseases, 2004, vol. 189, pp. 1221-1231.*

* cited by examiner

*Primary Examiner* — Robert C Hayes
(74) *Attorney, Agent, or Firm* — Judy Jarecki-Black; Duoying Chen; Merial Limited

(57) ABSTRACT

The present invention relates to an immunogenic or vaccine composition to induce an immune response or protective immune response against vesicular stomatitis virus (VSV) in an animal susceptible to VSV. The composition may include a pharmaceutically or veterinarily acceptable vehicle or excipient, and a vector. The vector may contain at least one heterologous nucleic acid molecule(s), expresses in vivo in the animal VSV antigen(s), immunogen(s) or epitope(s) thereof, e.g., VSV G protein and/or VSV N protein and/or VSV M protein. The heterologous nucleic acid molecule(s) may be adjusted to the vector/mammalian cell system by codon optimization. The composition can contain an adjuvant, such as carbomer. Methods for making and using such a composition, including prime-boost regimes and including as to differential diagnosis, are also contemplated.

9 Claims, 11 Drawing Sheets

FIGURE 1.

```
  1 TCACACAGGA AACAGCTATG ACCATGATTA CGAATTGCGG CCGCAATTCT
    AGTGTGTCCT TTGTCGATAC TGGTACTAAT GCTTAACGCC GGCGTTAAGA

51 GAATGTTAAA TGTTATACTT TGGATGAAGC TATAAATATG CATTGGAAAA
    CTTACAATTT ACAATATGAA ACCTACTTCG ATATTTATAC GTAACCTTTT

101 ATAATCCATT TAAAGAAAGG ATTCAAATAC TACAAACCT AAGCGATAAT
    TATTAGGTAA ATTTCTTTCC TAAGTTTATG ATGTTTGGA TTCGCTATTA

151 ATGTTAACTA AGCTTATTCT TAACGACGCT TTAAATATAC ACAAATAAAC
    TACAATTGAT TCGAATAAGA ATTGCTGCGA AATTTATATG TGTTTATTTG

201 ATAATTTTTG TATAACCTAA CAAATAACTA AAACATAAAA ATAATAAAAG
    TATTAAAAAC ATATTGGATT GTTATTGAT TTTGTATTTT TATTATTTTC

251 GAAATGTAAT ATCGTAATTA TTTTACTCAG GAATGGGGTT AAATATTTAT
    CTTTACATTA TAGCATTAAT AAAATGAGTC CTTACCCCAA TTTATAAATA

301 ATCACGTGTA TATCTATACT GTTATCGTAT ACTCTTTACA ATTACTATTA
    TAGTGCACAT ATAGATATGA CAATAGCATA TGAGAAATGT AATGATAAT

351 CGAATATGCA AGAGATAATA AGATTACGTA TTTAAGAGAA TCTTGTCATG
    GCTTATACGT TCTCTATTAT TCTAATGCAT AAATTCTCTT AGAACAGTAC

401 ATAATTGGGT ACGACATAGT GATAAATGCT ATTTCGCATC GTTACATAAA
    TATTAACCCA TGCTGTATCA CTATTTACGA TAAAGCGTAG CAATGTATTT

451 GTCAGTTGGA AAGATGGATT TGACAGATGT AACTTAATAG GTGCAAAAAT
    CAGTCAACCT TTCTACCTAA ACTGTCTACA TTGAATTATC CACGTTTTA

501 GTTAAATAAC AGCATTCTAT CGGAAGATAG GATACCAGTT ATATTATACA
    CAATTTATTG TCGTAAGATA GCCTTCTATC CTATGGTCAA TATAATATGT

551 AAAATCACTG GTTGGATAAA ACAGATTCTG CAATATTCGT AAAAGATGAA
    TTTTAGTGAC CAACCTATTT TGTCTAAGAC GTTATAAGCA TTTTCTACTT

601 GATTACTGCG AATTTGTAAA CTATGACAAT AAAAAGCCAT TTATCTCAAC
    CTAATGACGC TTAAACATTT GATACTGTTA TTTTTCGGTA AATAGAGTTG

651 GACATCGTGT AATTCTTCCA TGTTTTATGT ATGTGTTTCA GATATTATGA
    CTGTAGCACA TTAAGAAGGT ACAAATACA TACACAAAGT CTATAATACT

701 GATTACTATA AACTTTTTGT ATACTTATAT TCCGTAAACT ATATTAATCA
    CTAATGATAT TTGAAAAACA TATGAATATA AGGCATTTGA TATAATTAGT

751 TGAAGAAAAT GAAAAGTAT AGAAGCTGTT CACGAGCGGT TGTTGAAAAC
    ACTTCTTTTA CTTTTTCATA TCTTCGACAA GTGCTCGCCA ACAACTTTTG
```

FIGURE 1. (continued)

```
 801  AACAAAATTA TACATTCAAG ATGGCTTACA TATACGTCTG TGAGGCTATC
      TTGTTTTAAT ATGTAAGTTC TACCGAATGT ATATGCAGAC ACTCCGATAG

851  ATGGATAATG ACAATGCATC TCTAAATAGG TTTTTGGACA ATGGATTCGA
      TACCTATTAC TGTTACGTAG AGATTTATCC AAAAACCTGT TACCTAAGCT

901  CCCTAACACG GAATATGGTA CTCTACAATC TCCTCTTGAA ATGGCTGTAA
      GGGATTGTGC CTTATACCAT GAGATGTTAG AGGAGAACTT TACCGACATT

951  TGTTCAAGAA TACCGAGGCT ATAAAAATCT TGATGAGGTA TGGAGCTAAA
      ACAAGTTCTT ATGGCTCCGA TATTTTTAGA ACTACTCCAT ACCTCGATTT

1001  CCTGTAGTTA CTGAATGCAC AACTTCTTGT CTGCATGATG CGGTGTTGAG
      GGACATCAAT GACTTACGTG TTGAAGAACA GACGTACTAC GCCACAACTC

1051  AGACGACTAC AAAATAGTGA AAGATCTGTT GAAGAATAAC TATGTAAACA
      TCTGCTGATG TTTTATCACT TTCTAGACAA CTTCTTATTG ATACATTTGT

1101  ATGTTCTTTA CAGCGGAGGC TTTACTCCTT TGTGTTTGGC AGCTTACCTT
      TACAAGAAAT GTCGCCTCCG AAATGAGGAA ACACAAACCG TCGAATGGAA

1151  AACAAAGTTA ATTTGGTTAA ACTTCTATTG GCTCATTCGG CGGATGTAGA
      TTGTTTCAAT TAAACCAATT TGAAGATAAC CGAGTAAGCC GCCTACATCT

1201  TATTTCAAAC ACGGATCGGT TAACTCCTCT ACATATAGCC GTATCAAATA
      ATAAAGTTTG TGCCTAGCCA ATTGAGGAGA TGTATATCGG CATAGTTTAT

1251  AAAATTTAAC AATGGTTAAA CTTCTATTGA ACAAAGGTGC TGATACTGAC
      TTTTAAATTG TTACCAATTT GAAGATAACT TGTTTCCACG ACTATGACTG

1301  TTGCTGGATA ACATGGGACG TACTCCTTTA ATGATCGCTG TACAATCTGG
      AACGACCTAT TGTACCCTGC ATGAGGAAAT TACTAGCGAC ATGTTAGACC

1351  AAATATTGAA ATATGTAGCA CACTACTTAA AAAAAATAAA ATGTCCAGAA
      TTTATAACTT TATACATCGT GTGATGAATT TTTTTATTT TACAGGTCTT

1401  CTGGGAAAAA TTGATCTTGC CAGCTGTAAT TCATGGTAGA AAAGAAGTGC
      GACCCTTTTT AACTAGAACG GTCGACATTA AGTACCATCT TTTCTTCACG

1451  TCAGGCTACT TTTCAACAAA GGAGCAGATG TAAACTACAT CTTTGAAAGA
      AGTCCGATGA AAAGTTGTTT CCTCGTCTAC ATTTGATGTA GAAACTTTCT

1501  AATGGAAAAT CATATACTGT TTTGGAATTG ATTAAAGAAA GTTACTCTGA
      TTACCTTTTA GTATATGACA AAACCTTAAC TAATTTCTTT CAATGAGACT

1551  GACACAAAAG AGGTAGCTGA AGTGGTACTC TCAAAGGTAC GTGACTAATT
      CTGTGTTTTC TCCATCGACT TCACCATGAG AGTTTCCATG CACTGATTAA

1601  AGCTATAAAA AGGATCCGGG TTAATTAATT AGTCATCAGG CAGGGCGAGA
      TCGATATTTT TCCTAGGCCC AATTAATTAA TCAGTAGTCC GTCCCGCTCT

1651  ACGAGACTAT CTGCTCGTTA ATTAATTAGA GCTTCTTTAT TCTATACTTA
      TGCTCTGATA GACGAGCAAT TAATTAATCT CGAAGAAATA AGATATGAAT
```

FIGURE 1. (Continued)

```
1701 AAAAGTGAAA ATAAATACAA AGGTTCTTGA GGGTTGTGTT AAATTGAAAG
     TTTTCACTTT TATTTATGTT TCCAAGAACT CCCAACACAA TTTAACTTTC

1751 CGAGAAATAA TCATAAATTA TTTCATTATC GCGATATCCG TTAAGTTTGT
     GCTCTTTATT AGTATTTAAT AAAGTAATAG CGCTATAGGC AATTCAAACA

MetLeu SerTyrLeu IleLeuAla IleIleValSer ProIleLeu·
1801 ATCGTAATGC TGTCCTACCT GATCCTGGCC ATCATCGTGT CCCCTATCCT
     TAGCATTACG ACAGGATGGA CTAGGACCGG TAGTAGCACA GGGGATAGGA

·GlyLysIle GluIleValPhe ProGlnHis ThrThrGly AspTrpLysArg·
1851 GGGCAAGATC GAGATCGTGT TCCCCCAGCA CACCACCGGC GATTGGAAGA
     CCCGTTCTAG CTCTAGCACA AGGGGGTCGT GTGGTGGCCG CTAACCTTCT

·AValProHis GluTyrAsn TyrCysProThr SerAlaAsp LysAsnSer·
1901 GAGTGCCCCA CGAGTACAAC TACTGCCCTA CCAGCGCCGA CAAGAATAGC
     CTCACGGGGT GCTCATGTTG ATGACGGGAT GGTCGCGGCT GTTCTTATCG

HisGlyThrGln ThrGlyIle ProValGlu LeuThrMetPro LysGlyLeu·
1951 CACGGCACCC AGACCGGCAT CCCCGTGGAG CTGACCATGC CCAAGGGCCT
     GTGCCGTGGG TCTGGCCGTA GGGGCACCTC GACTGGTACG GGTTCCCGGA

·ThrThrHis GlnValAspGly PheMetCys HisSerAla LeuTrpMetThr·
2001 GACCACCCAC CAGGTGGACG GCTTCATGTG CCACAGCGCC CTGTGGATGA
     CTGGTGGGTG GTCCACCTGC CGAAGTACAC GGTGTCGCGG GACACCTACT

·TThrCysAsp PheArgTrp TyrGlyProLys TyrIleThr HisSerIle
2051 CCACCTGTGA CTTCAGATGG TACGGCCCCA AGTACATCAC CCACAGCATC
     GGTGGACACT GAAGTCTACC ATGCCGGGGT TCATGTAGTG GGTGTCGTAG

HisAsnGluGlu ProThrAsp TyrGlnCys LeuGluAlaIle LysAlaTyr·
2101 CACAACGAGG AGCCCACCGA TTACCAGTGC CTGGAGGCCA TCAAGGCCTA
     GTGTTGCTCC TCGGGTGGCT AATGGTCACG GACCTCCGGT AGTTCCGGAT

·LysAspGly ValGlyPheAsn ProGlyPhe ProProGln SerCysGlyTyr·
2151 CAAGGACGGA GTGGGCTTCA ATCCTGGCTT CCCCCCCCAG AGCTGTGGCT
     GTTCCTGCCT CACCCGAAGT TAGGACCGAA GGGGGGGGTC TCGACACCGA

·TGlyThrVal ThrAspAla GluAlaHisIle IleThrVal ThrProHis
2201 ACGGCACCGT GACCGACGCC GAGGCCCACA TCATCACCGT GACCCCCCAC
     TGCCGTGGCA CTGGCTGCGG CTCCGGGTGT AGTAGTGGCA CTGGGGGGTG

SerValLysVal AspGluTyr ThrGlyGlu TrpIleAspPro HisPheIle·
2251 AGCGTGAAGG TGGACGAGTA CACCGGCGAG TGGATCGACC CCCACTTCAT
     TCGCACTTCC ACCTGCTCAT GTGGCCGCTC ACCTAGCTGG GGGTGAAGTA

·GlyGlyArg CysLysGlyLys IleCysGlu ThrValHis AsnSerThrLys·
2301 CGGCGGCAGG TGTAAGGGCA AAATCTGTGA GACCGTGCAC AACAGCACCA
     GCCGCCGTCC ACATTCCCGT TTTAGACACT CTGGCACGTG TTGTCGTGGT

·LTrpPheThr SerSerAsp GlyGluSerVal CysSerGln LeuPheThr
2351 AGTGGTTCAC CAGCAGCGAC GGCGAGAGCG TGTGTAGCCA GCTGTTCACC
     TCACCAAGTG GTCGTCGCTG CCGCTCTCGC ACACATCGGT CGACAAGTGG
```

FIGURE 1. (Continued)

```
            LeuValGlyGly ThrPhePhe SerAspSer GluGluIleThr SerMetGly·
     2401   CTGGTGGGCG GCACCTTCTT CAGCGACAGC GAGGAGATCA CCAGCATGGG
            GACCACCCGC CGTGGAAGAA GTCGCTGTCG CTCCTCTAGT GGTCGTACCC

·LeuProGlu ThrGlyIleArg SerAsnTyr PheProTyr IleSerThrGlu·
     2451   CCTGCCCGAG ACAGGCATCC GGAGCAACTA CTTCCCCTAC ATCAGCACCG
            GGACGGGCTC TGTCCGTAGG CCTCGTTGAT GAAGGGGATG TAGTCGTGGC

·GGlyIleCys LysMetPro PheCysArgLys ProGlyTyr LysLeuLys
     2501   AGGGCATCTG TAAGATGCCA TTTTGCCGGA AGCCTGGCTA CAAGCTGAAG
            TCCCGTAGAC ATTCTACGGT AAAACGGCCT TCGGACCGAT GTTCGACTTC

AsnAspLeuTrp PheGlnIle ThrAspPro AspLeuAspLys ThrValArg·
     2551   AACGACCTGT GGTTCCAGAT CACCGACCCC GACCTGGACA AGACAGTGAG
            TTGCTGGACA CCAAGGTCTA GTGGCTGGGG CTGGACCTGT TCTGTCACTC

·AspLeuPro HisIleLysAsp CysAspLeu SerSerSer IleIleThrPro·
     2601   AGACCTGCCC CACATCAAGG ACTGTGACCT GAGCAGCAGC ATCATCACCC
            TCTGGACGGG GTGTAGTTCC TGACACTGGA CTCGTCGTCG TAGTAGTGGG

·PGlyGluHis AlaThrAsp IleSerLeuIle SerAspVal GluArgIle
     2651   CTGGCGAGCA CGCCACCGAT ATCAGCCTGA TCAGCGACGT GGAGCGGATC
            GACCGCTCGT GCGGTGGCTA TAGTCGGACT AGTCGCTGCA CCTCGCCTAG

LeuAspTyrAla LeuCysGln AsnThrTrp GlyLysIleGlu AlaGlyGlu·
     2701   CTGGACTACG CCCTGTGCCA GAATACCTGG GGGAAGATCG AGGCCGGCGA
            GACCTGATGC GGGACACGGT CTTATGGACC CCCTTCTAGC TCCGGCCGCT

·ProIleThr ProValAspLeu SerTyrLeu GlyProLys AsnProGlyVal·
     2751   GCCCATCACC CCCGTGGACC TGAGCTACCT GGGCCCTAAG AATCCCGGAG
            CGGGTAGTGG GGGCACCTGG ACTCGATGGA CCCGGGATTC TTAGGGCCTC

·VGlyProVal PheThrIle IleAsnSerSer LeuHisTyr PheThrSer
     2801   TGGGCCCTGT GTTCACCATC ATCAACAGCA GCCTGCACTA CTTCACCAGC
            ACCCGGGACA CAAGTGGTAG TAGTTGTCGT CGGACGTGAT GAAGTGGTCG

LysTyrLeuArg ValGluLeu GluSerPro ValIleProArg MetGluGly·
     2851   AAGTACCTGA GGGTGGAGCT GGAGAGCCCT GTGATCCCTA GGATGGAGGG
            TTCATGGACT CCCACCTCGA CCTCTCGGGA CACTAGGGAT CCTACCTCCC

·ArgValAla GlyThrArgIle ValArgGln LeuTrpAsp GlnTrpPhePro·
     2901   CAGAGTGGCC GGCACCAGGA TTGTGAGACA GCTGTGGGAC CAGTGGTTCC
            GTCTCACCGG CCGTGGTCCT AACACTCTGT CGACACCCTG GTCACCAAGG

·PPheGlyGlu AlaGluIle GlyProAsnGly ValLeuLys ThrLysGln
     2951   CCTTCGGCGA GGCCGAGATC GGCCCCAACG GCGTGCTGAA AACCAAGCAG
            GGAAGCCGCT CCGGCTCTAG CCGGGGTTGC CGCACGACTT TTGGTTCGTC

GlyTyrLysPhe ProLeuHis IleIleGly ThrGlyGluVal AspSerAsp·
     3001   GGCTACAAGT TCCCCCTGCA CATCATCGGC ACAGGCGAGG TGGACAGCGA
            CCGATGTTCA AGGGGGACGT GTAGTAGCCG TGTCCGCTCC ACCTGTCGCT

·IleLysMet GluArgIleVal LysHisTrp GluHisPro HisIleGluAla·
     3051   CATCAAGATG GAGAGGATCG TGAAGCACTG GGAGCACCCT CACATCGAGG
            GTAGTTCTAC CTCTCCTAGC ACTTCGTGAC CCTCGTGGGA GTGTAGCTCC
```

FIGURE 1. (Continued)

```
             ·AAlaGlnThr TyrLeuLys LysAspAspThr GluGluVal IleTyrTyr
      3101 CCGCCCAGAC CTACCTGAAG AAGGACGACA CCGAGGAGGT GATCTACTAC
           GGCGGGTCTG GATGGACTTC TTCCTGCTGT GGCTCCTCCA CTAGATGATG

GlyAspThrGly IleSerLys AsnProVal GluLeuValGlu GlyTrpPhe·
      3151 GGCGACACCG GCATCAGCAA GAACCCTGTG GAACTGGTGG AGGGCTGGTT
           CCGCTGTGGC CGTAGTCGTT CTTGGGACAC CTTGACCACC TCCCGACCAA

·SerGlyTrp ArgSerSerIle MetGlyVal ValAlaVal IleIleGlyPhe·
      3201 CAGCGGCTGG AGGAGCAGCA TTATGGGCGT GGTGGCCGTG ATCATCGGCT
           GTCGCCGACC TCCTCGTCGT AATACCCGCA CCACCGGCAC TAGTAGCCGA

·PValIleLeu IlePheLeu IleArgLeuIle GlyValLeu SerSerLeu
      3251 TCGTGATCCT GATCTTCCTG ATCCGGCTGA TCGGCGTGCT GTCCAGCCTG
           AGCACTAGGA CTAGAAGGAC TAGGCCGACT AGCCGCACGA CAGGTCGGAC

PheArgProLys ArgArgPro IleTyrLys SerAspValGlu MetAlaHis·
      3301 TTCCGGCCTA AGCGGAGGCC TATCTACAAG TCCGACGTGG AGATGGCCCA
           AAGGCCGGAT TCGCCTCCGG ATAGATGTTC AGGCTGCACC TCTACCGGGT

·PheArg***
      3351 CTTCCGGTGA TGATTTTTAT GACTAGTTAA TCACGGCCGC TTATAAAGAT
           GAAGGCCACT ACTAAAAATA CTGATCAATT AGTGCCGGCG AATATTTCTA

3401 CTAAAATGCA TAATTTCTAA ATAATGAAAA AAAGTACATC ATGAGCAACG
           GATTTTACGT ATTAAAGATT TATTACTTTT TTTCATGTAG TACTCGTTGC

3451 CGTTAGTATA TTTTACAATG GAGATTAACG CTCTATACCG TTCTATGTTT
           GCAATCATAT AAAATGTTAC CTCTAATTGC GAGATATGGC AAGATACAAA

3501 ATTGATTCAG ATGATGTTTT AGAAAAGAAA GTTATTGAAT ATGAAACTT
           TAACTAAGTC TACTACAAAA TCTTTTCTTT CAATAACTTA TACTTTGAA

3551 TAATGAAGAT GAAGATGACG ACGATGATTA TTGTTGTAAA TCTGTTTTAG
           ATTACTTCTA CTTCTACTGC TGCTACTAAT AACAACATTT AGACAAAATC

3601 ATGAAGAAGA TGACGCGCTA AAGTATACTA TGGTTACAAA GTATAAGTCT
           TACTTCTTCT ACTGCGCGAT TCATATGAT ACCAATGTTT CATATTCAGA

3651 ATACTACTAA TGGCGACTTG TGCAAGAAGG TATAGTATAG TGAAAATGTT
           TATGATGATT ACCGCTGAAC ACGTTCTTCC ATATCATATC ACTTTTACAA

3701 GTTAGATTAT GATTATGAAA AACCAAATAA ATCAGATCCA TATCTAAAGG
           CAATCTAATA CTAATACTTT TTGGTTTATT TAGTCTAGGT ATAGATTTCC

3751 TATCTCCTTT GCACATAATT TCATCTATTC CTAGTTTAGA ATACCTGCAG
           ATAGAGGAAA CGTGTATTAA AGTAGATAAG GATCAAATCT TATGGACGTC

3801 CCAAGCTTGG CACTGGCCGT CGTTTTACA
           GGTTCGAACC GTGACCGGCA GCAAAATGT
```

FIGURE 2.

```
   1   GGAAACAGCT ATGACCATGA TTACGAATTG CGGCCGCAAT TCTGAATGTT AAATGTTATA
       CCTTTGTCGA TACTGGTACT AATGCTTAAC GCCGGCGTTA AGACTTACAA TTTACAATAT

61   CTTTGGATGA AGCTATAAAT ATGCATTGGA AAAATAATCC ATTTAAAGAA AGGATTCAAA
       GAAACCTACT TCGATATTTA TACGTAACCT TTTTATTAGG TAAATTTCTT TCCTAAGTTT

121   TACTACAAAA CCTAAGCGAT AATATGTTAA CTAAGCTTAT TCTTAACGAC GCTTTAAATA
       ATGATGTTTT GGATTCGCTA TTATACAATT GATTCGAATA AGAATTGCTG CGAAATTTAT

181   TACACAAATA AACATAATTT TTGTATAACC TAACAAATAA CTAAAACATA AAAATAATAA
       ATGTGTTTAT TTGTATTAAA AACATATTGG ATTGTTTATT GATTTTGTAT TTTTATTATT

241   AAGGAAATGT AATATCGTAA TTATTTTACT CAGGAATGGG GTTAAATATT TATATCACGT
       TTCCTTTACA TTATAGCATT AATAAAATGA GTCCTTACCC CAATTTATAA ATATAGTGCA

301   GTATATCTAT ACTGTTATCG TATACTCTTT ACAATTACTA TTACGAATAT GCAAGAGATA
       CATATAGATA TGACAATAGC ATATGAGAAA TGTTAATGAT AATGCTTATA CGTTCTCTAT

361   ATAAGATTAC GTATTTAAGA GAATCTTGTC ATGATAATTG GGTACGACAT AGTGATAAAT
       TATTCTAATG CATAAATTCT CTTAGAACAG TACTATTAAC CCATGCTGTA TCACTATTTA

421   GCTATTTCGC ATCGTTACAT AAAGTCAGTT GGAAAGATGG ATTTGACAGA TGTAACTTAA
       CGATAAAGCG TAGCAATGTA TTTCAGTCAA CCTTTCTACC TAAACTGTCT ACATTGAATT

481   TAGGTGCAAA AATGTTAAAT AACAGCATTC TATCGGAAGA TAGGATACCA GTTATATTAT
       ATCCACGTTT TTACAATTTA TTGTCGTAAG ATAGCCTTCT ATCCTATGGT CAATATAATA

541   ACAAAAATCA CTGGTTGGAT AAAACAGATT CTGCAATATT CGTAAAAGAT GAAGATTACT
       TGTTTTTAGT GACCAACCTA TTTTGTCTAA GACGTTATAA GCATTTTCTA CTTCTAATGA

601   GCGAATTTGT AAACTATGAC AATAAAAAGC CATTTATCTC AACGCACATCG TGTAATTCTT
       CGCTTAAACA TTTGATACTG TTATTTTTCG GTAAATAGAG TTGCTGTAGC ACATTAAGAA

661   CCATGTTTTA TGTATGTGTT TCAGATATTA TGAGATTACT ATAAACTTTT TGTATACTTA
       GGTACAAAAT ACATACACAA AGTCTATAAT ACTCTAATGA TATTTGAAAA ACATATGAAT

721   TATTCCGTAA ACTATATTAA TCATGAAGAA AATGAAAAAG TATAGAAGCT GTTCACGAGC
       ATAAGGCATT TGATATAATT AGTACTTCTT TTACTTTTTC ATATCTTCGA CAAGTGCTCG

781   GGTTGTTGAA AACAACAAAA TTATACATTC AAGATGGCTT ACATATACGT CTGTGAGGCT
       CCAACAACTT TTGTTGTTTT AATATGTAAG TTCTACCGAA TGTATATGCA GACACTCCGA

841   ATCATGGATA ATGACAATGC ATCTCTAAAT AGGTTTTTGG ACAATGGATT CGACCCTAAC
       TAGTACCTAT TACTGTTACG TAGAGATTTA TCCAAAAACC TGTTACCTAA GCTGGGATTG

901   ACGGAATATG GTACTCTACA ATCTCCTCTT GAAATGGCTG TAATGTTCAA GAATACCGAG
       TGCCTTATAC CATGAGATGT TAGAGGAGAA CTTTACCGAC ATTACAAGTT CTTATGGCTC

961   GCTATAAAAA TCTTGATGAG GTATGGAGCT AAACCTGTAG TTACTGAATG CACAACTTCT
       CGATATTTTT AGAACTACTC CATACCTCGA TTTGGACATC AATGACTTAC GTGTTGAAGA

1021   TGTCTGCATG ATGCGGTGTT GAGAGACGAC TACAAAATAG TGAAAGATCT GTTGAAGAAT
       ACAGACGTAC TACGCCACAA CTCTCTGCTG ATGTTTATC  ACTTCTAGA CAACTTCTTA

1081   AACTATGTAA ACAATGTTCT TTACAGCGGA GGCTTTACTC CTTTGTGTTT GGCAGCTTAC
```

FIGURE 2. (Continued)

```
        TTGATACATT TGTTACAAGA AATGTCGCCT CCGAAATGAG GAAACACAAA CCGTCGAATG
1141    CTTAACAAAG TTAATTTGGT TAAACTTCTA TTGGCTCATT CGGCGGATGT AGATATTTCA
        GAATTGTTTC AATTAAACCA ATTTGAAGAT AACCGAGTAA GCCGCCTACA TCTATAAAGT

1201    AACACGGATC GGTTAACTCC TCTACATATA GCCGTATCAA ATAAAAATTT AACAATGGTT
        TTGTGCCTAG CCAATTGAGG AGATGTATAT CGGCATAGTT TATTTTAAA TTGTTACCAA

1261    AAACTTCTAT TGAACAAAGG TGCTGATACT GACTTGCTGG ATAACATGGG ACGTACTCCT
        TTTGAAGATA ACTTGTTTCC ACGACTATGA CTGAACGACC TATTGTACCC TGCATGAGGA

1321    TTAATGATCG CTGTACAATC TGGAAATATT GAAATATGTA GCACACTACT TAAAAAAAAT
        AATTACTAGC GACATGTTAG ACCTTTATAA CTTTATACAT CGTGTGATGA ATTTTTTTA

1381    AAAATGTCCA GAACTGGGAA AAATTGATCT TGCCAGCTGT AATTCATGGT AGAAAAGAAG
        TTTTACAGGT CTTGACCCTT TTTAACTAGA ACGGTCGACA TTAAGTACCA TCTTTTCTTC

1441    TGCTCAGGCT ACTTTTCAAC AAAGGAGCAG ATGTAAACTA CATCTTTGAA AGAAATGGAA
        ACGAGTCCGA TGAAAAGTTG TTTCCTCGTC TACATTTGAT GTAGAAACTT TCTTTACCTT

1501    AATCATATAC TGTTTTGGAA TTGATTAAAG AAAGTTACTC TGAGACACAA AAGAGGTAGC
        TTAGTATATG ACAAAACCTT AACTAATTTC TTTCAATGAG ACTCTGTGTT TTCTCCATCG

1561    TGAAGTGGTA CTCTCAAAGG TACGTGACTA ATTAGCTATA AAAAGGATCC GGGTTAATTA
        ACTTCACCAT GAGAGTTTCC ATGCACTGAT TAATCGATAT TTTTCCTAGG CCCAATTAAT

1621    ATTAGTCATC AGGCAGGGCG AGAACGAGAC TATCTGCTCG TTAATTAATT AGAGCTTCTT
        TAATCAGTAG TCCGTCCCGC TCTTGCTCTG ATAGACGAGC AATTAATTAA TCTCGAAGAA

1681    TATTCTATAC TTAAAAAGTG AAAATAAATA CAAAGGTTCT TGAGGGTTGT GTTAAATTGA
        ATAAGATATG AATTTTTCAC TTTTATTTAT GTTTCCAAGA ACTCCCAACA CAATTTAACT
                                                                        M
1741    AAGCGAGAAA TAATCATAAA TTATTTCATT ATCGCGATAT CCGTTAAGTT TGTATCGTAA
        TTCGCTCTTT ATTAGTATTT AATAAAGTAA TAGCGCTATA GGCAATTCAA ACATAGCATT

.. K  C  L    L  Y  L    A  F  L    S  I  G    V  N  C    K  F  T  I  V
1801    TGAAGTGCCT GCTGTACCTG GCCTTCCTGA GCATCGGCGT GAACTGCAAG TTCACCATCG
        ACTTCACGGA CGACATGGAC CGGAAGGACT CGTAGCCGCA CTTGACGTTC AAGTGGTAGC

.. F  P  H    N  Q  K    G  T  W    K  N  V    P  S  N  Y    H  Y  C  P
1861    TGTTCCCCCA CAACCAGAAG GGCACCTGGA AGAACGTGCC CAGCAACTAC CACTACTGCC
        ACAAGGGGGT GTTGGTCTTC CCGTGGACCT TCTTGCACGG GTCGTTGATG GTGATGACGG

.. S  S  S    D  L  N    W  H  N  D    L  I  G    T  A  L    Q  V  K  M
1921    CCAGCAGCAG CGATCTGAAC TGGCACAACG ACCTGATCGG CACCGCCCTG CAGGTGAAGA
        GGTCGTCGTC GCTAGACTTG ACCGTGTTGC TGGACTAGCC GTGGCGGGAC GTCCACTTCT

.. P  K  S    H  K  A    I  Q  A  D    G  W  M    C  H  A    S  K  W  V
1981    TGCCCAAGAG CCACAAGGCC ATCCAGGCCG ACGGCTGGAT GTGCCACGCC AGCAAGTGGG
        ACGGGTTCTC GGTGTTCCGG TAGGTCCGGC TGCCGACCTA CACGGTGCGG TCGTTCACCC

.. T  T  C    D  F  R    W  Y  G  P    K  Y  I    T  H  S    I  R  S  F
2041    TGACCACCTG CGACTTCAGA TGGTACGGCC CCAAGTACAT CACCCACAGC ATCAGGAGCT
        ACTGGTGGAC GCTGAAGTCT ACCATGCCGG GGTTCATGTA GTGGGTGTCG TAGTCCTCGA

.. T  P  S    V  E  Q    C  R  E  S    I  E  Q    T  K  Q    G  T  W  L
2101    TCACCCCTAG CGTGGAGCAG TGCAGGGAGA GCATCGAGCA GACCAAGCAG GGCACATGGC
        AGTGGGGATC GCACCTCGTC ACGTCCCTCT CGTAGCTCGT CTGGTTCGTC CCGTGTACCG
```

FIGURE 2. (Continued)

```
           ..N  P  G    F  P  P     Q  S  C    G  Y  A  T    V  T  D    A  E  A  V
2161       TGAATCCTGG  CTTCCCTCCC  CAGAGCTGCG  GCTACGCCAC  CGTGACCGAC  GCCGAGGCCG
           ACTTAGGACC  GAAGGGAGGG  GTCTCGACGC  CGATGCGGTG  GCACTGGCTG  CGGCTCCGGC

..I  V  Q    V  T  P    H  H  V    L  V  D  E    Y  T  G    E  W  V  D
2221       TGATCGTGCA  GGTGACCCCC  CACCACGTGC  TGGTCGATGA  GTACACCGGC  GAGTGGGTGG
           ACTAGCACGT  CCACTGGGGG  GTGGTGCACG  ACCAGCTACT  CATGTGGCCG  CTCACCCACC

..S  Q  F    I  N  G    K  C  S  N    D  I  C    P  T  V    H  N  S  T
2281       ACAGCCAGTT  CATCAACGGC  AAGTGCAGCA  ACGACATCTG  CCCCACCGTG  CACAACAGCA
           TGTCGGTCAA  GTAGTTGCCG  TTCACGTCGT  TGCTGTAGAC  GGGGTGGCAC  GTGTTGTCGT

..T  W  H    S  D  Y    K  V  K  G    L  C  D    S  N  L    I  S  M  D
2341       CCACCTGGCA  CAGCGACTAC  AAAGTGAAGG  GCCTGTGCGA  CAGCAACCTG  ATCAGCATGG
           GGTGGACCGT  GTCGCTGATG  TTTCACTTCC  CGGACACGCT  GTCGTTGGAC  TAGTCGTACC

..I  T  F    F  S  E    D  G  E  L    S  S  L    G  K  E    G  T  G  F
2401       ACATCACCTT  TTTCAGCGAG  GACGGCGAGC  TGAGCAGCCT  GGGCAAGGAG  GGCACCGGCT
           TGTAGTGGAA  AAAGTCGCTC  CTGCCGCTCG  ACTCGTCGGA  CCCGTTCCTC  CCGTGGCCGA

..R  S  N    H  F  A    Y  E  T  G    D  K  A    C  K  M    Q  Y  C  K
2461       TCAGAAGCAA  CCACTTCGCC  TACGAGACCG  GCGACAAGGC  CTGCAAGATG  CAGTACTGCA
           AGTCTTCGTT  GGTGAAGCGG  ATGCTCTGGC  CGCTGTTCCG  GACGTTCTAC  GTCATGACGT

..H  W  G    V  R  L    P  S  G  V    W  F  E    M  A  D    Q  D  L  F
2521       AGCACTGGGG  AGTGAGACTG  CCCAGCGGCG  TGTGGTTCGA  GATGGCCGAC  CAGGACCTGT
           TCGTGACCCC  TCACTCTGAC  GGGTCGCCGC  ACACCAAGCT  CTACCGGCTG  GTCCTGGACA

..A  A  A    R  F  P    E  C  P  E    G  S  S    I  S  A    P  S  Q  T
2581       TCGCCGCCGC  CAGATTCCCC  GAGTGCCCCG  AGGGCAGCAG  CATCAGCGCC  CCCAGCCAGA
           AGCGGCGGCG  GTCTAAGGGG  CTCACGGGGC  TCCCGTCGTC  GTAGTCGCGG  GGGTCGGTCT

..S  V  D    V  S  L    I  Q  D  V    E  R  I    L  D  Y    S  L  C  Q
2641       CCAGCGTGGA  TGTGAGCCTG  ATCCAGGACG  TGGAGCGGAT  CCTGGATTAC  AGCCTGTGCC
           GGTCGCACCT  ACACTCGGAC  TAGGTCCTGC  ACCTCGCCTA  GGACCTAATG  TCGGACACGG

..E  T  W    S  K  I    G  A  G  L    P  I  S    P  V  D    L  S  Y  L
2701       AGGAGACCTG  GAGCAAGATC  GGAGCCGGCC  TGCCCATCAG  CCCCGTGGAC  CTGAGCTACC
           TCCTCTGGAC  CTCGTTCTAG  CCTCGGCCGG  ACGGGTAGTC  GGGGCACCTG  GACTCGATGG

..A  P  K    N  P  G    T  G  P  A    F  T  I    I  N  G    T  L  K  Y
2761       TGGCCCCTAA  GAACCCCGGC  ACCGGCCCAG  CCTTCACCAT  CATCAACGGG  ACCCTGAAGT
           ACCGGGGATT  CTTGGGGCCG  TGGCCGGGTC  GGAAGTGGTA  GTAGTTGCCC  TGGGACTTCA

..F  E  T    R  Y  I    R  V  D  I    A  A  P    I  L  S    R  M  V  G
2821       ACTTCGAGAC  CCGGTACATC  AGAGTGGACA  TTGCCGCCCC  TATCCTGAGC  AGAATGGTGG
           TGAAGCTCTG  GGCCATGTAG  TCTCACCTGT  AACGGCGGGG  ATAGGACTCG  TCTTACCACC

..M  I  S    G  T  T    T  E  R  E    L  W  D    D  W  A    P  Y  E  D
2881       GCATGATCAG  CGGCACCACC  ACCGAGAGAG  AGCTGTGGGA  CGATTGGGCC  CCTTACGAGG
           CGTACTAGTC  GCCGTGGTGG  TGGCTCTCTC  TCGACACCCT  GCTAACCCGG  GGAATGCTCC

..V  E  I    G  P  N    G  V  L  R    T  S  S    G  Y  K    F  P  L  Y
2941       ATGTGGAGAT  CGGCCCTAAC  GGCGTGCTGA  GAACCAGCAG  CGGCTACAAG  TTCCCCCTGT
           TACACCTCTA  GCCGGGATTG  CCGCACGACT  CTTGGTCGTC  GCCGATGTTC  AAGGGGGACA

..M  I  G    H  G  M    L  D  S  D    I  H  L    S  S  K    A  Q  V  F
3001       ACATGATCGG  CCACGGCATG  CTGGACAGCG  ACCTGCACCT  GAGCAGCAAG  GCCCAGGTGT
           TGTACTAGCC  GGTGCCGTAC  GACCTGTCGC  TGGACGTGGA  CTCGTCGTTC  CGGGTCCACA
```

FIGURE 2. (Continued)

```
        ..E  H  P    H  I  Q    D  A  A  S    Q  L  P    D  D  E    T  L  F  F
3061    TCGAGCACCC CCACATCCAG GACGCCGCCA GCCAGCTGCC CGACGACGAG ACCCTGTTCT
        AGCTCGTGGG GGTGTAGGTC CTGCGGCGGT CGGTCGACGG GCTGCTGCTC TGGGACAAGA

..G  D  T    G  L  S    K  N  P  I    E  L  V    E  G  W    F  S  G  W
3121    TCGGCGACAC CGGCCTGAGC AAGAACCCTA TCGAACTGGT GGAGGGCTGG TTCAGCGGCT
        AGCCGCTGTG GCCGGACTCG TTCTTGGGAT AGCTTGACCA CCTCCCGACC AAGTCGCCGA

..K  S  S    I  A  S    F  F  F  I    G  L    I  I  G    L  F  L  V
3181    GGAAGAGCAG CATCGCCAGC TTCTTCTTCA TCATCGGCCT GATCATCGGG CTGTTTCTGG
        CCTTCTCGTC GTAGCGGTCG AAGAAGAAGT AGTAGCCGGA CTAGTAGCCC GACAAAGACC

..L  R  V    G  I  Y    L  C  I  K    L  K  H    T  K  K    R  Q  I  Y
3241    TGCTGAGAGT GGGCATCTAC CTGTGCATCA AGCTGAAGCA CACCAAGAAG CGGCAAATCT
        ACGACTCTCA CCCGTAGATG GACACGTAGT TCGACTTCGT GTGGTTCTTC GCCGTTTAGA

..T  D  I    E  M  N    R  L  G  K
3301    ACACCGACAT CGAGATGAAC CGGCTGGGCA AGTGATGATA GCTCGAGTCT AGAATCGATC
        TGTGGCTGTA GCTCTACTTG GCCGACCCGT TCACTACTAT CGAGCTCAGA TCTTAGCTAG

3361    CCGGGTTTTT ATGACTAGTT AATCACGGCC GCTTATAAAG ATCTAAAATG CATAATTTCT
        GGCCCAAAAA TACTGATCAA TTAGTGCCGG CGAATATTTC TAGATTTTAC GTATTAAAGA

3421    AAATAATGAA AAAAGTACA  TCATGAGCAA CGCGTTAGTA TATTTTACAA TGGAGATTAA
        TTTATTACTT TTTTCATGT  AGTACTCGTT GCGCAATCAT ATAAAATGTT ACCTCTAATT

3481    CGCTCTATAC CGTTCTATGT TTATTGATTC AGATGATGTT TTAGAAAAGA AAGTTATTGA
        GCGAGATATG GCAAGATACA AATAACTAAG TCTACTACAA AATCTTTTCT TTCAATAACT

3541    ATATGAAAAC TTAATGAAG  ATGAAGATGA CGACGATGAT TATTGTTGTA AATCTGTTTT
        TATACTTTTG AAATTACTTC TACTTCTACT GCTGCTACTA ATAACAACAT TTAGACAAAA

3601    AGATGAAGAA GATGACGCGC TAAAGTATAC TATGGTTACA AAGTATAAGT CTATACTACT
        TCTACTTCTT CTACTGCGCG ATTTCATATG ATACCAATGT TTCATATTCA GATATGATGA

3661    AATGGCGACT TGTGCAAGAA GGTATAGTAT AGTGAAAATG TTGTTAGATT ATGATTATGA
        TTACCGCTGA ACACGTTCTT CCATATCATA TCACTTTTAC AACAATCTAA TACTAATACT

3721    AAAACCAAAT AAATCAGATC CATATCTAAA GGTATCTCCT TTGCACATAA TTTCATCTAT
        TTTTGGTTTA TTTAGTCTAG GTATAGATTT CCATAGAGGA AACGTGTATT AAAGTAGATA

3781    TCCTAGTTTA GAATACCTGC AGCCAAGCTT GGCACTGGCC GTCGTTTTAC AACGTCGTGA
        AGGATCAAAT CTTATGGACG TCGGTTCGAA CCGTGACCGG CAGCAAAATG TTGCAGCACT
```

Western blot analysis of primary chicken embryonic fibroblasts infected with vCP2300.

1. PageRuler Prestained Protein Ladder
2. vCP2300.2.6.1.1 Cell Lysate
3. ALVAC Cell Lysate
4. vCP2300.2.6.1.3 Cell Lysate
5. vCP2300.2.6.1.1 Supernatant
6. ALVAC Supernatant
7. vCP2300.2.6.1.3 Supernatant

Western blot analysis of primary chicken embryonic fibroblasts infected with vCP2298

Anti-VSV G, 1/200 dilution, 1 min exposure

← VSV G 1. 7 µl Fermentas PageRuler
2. Space
3. 30 µl ALVAC cell pellet
4. 30 µl vCP2298 cell pellet
5. Space
6. 40 µl ALVAC culture supernatant
7. 40 µl vCP2298 culture

VACCINES AGAINST VESICULAR STOMATITIS

This application claims priority to US Provisional Patent Application 60/833,208 filed Jul. 25, 2006.

Each of the above applications, together with each document cited therein, and each of the documents referenced or cited in documents cited therein, are hereby incorporated herein by reference.

Each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

FIELD OF THE INVENTION

The invention relates to in vivo expression vectors encoding and expressing at least one vesicular stomatitis virus (VSV) immunogen, to the use of such vectors for the production of vaccines and to these vaccines.

BACKGROUND OF THE INVENTION

Vesicular stomatitis virus (VSV), a member in the rhabdoviridae family, causes a contagious disease in horses, cattle, pigs, sheep and goats, characterized by vesicular lesions on the tongue, oral mucosa and udder. VSV is transmitted by arthropod vectors. The prominent clinical presentation of vesicular stomatitis is the development of vesicles and ulcers in the oral cavity and, less frequently, on the teats and coronary bands. Mortality rates are typically very low, but production suffers because affected animals lose weight and may develop lameness or mastitis. The most significant concern with vesicular stomatitis is that, in cattle and pigs, it is clinically indistinguishable from foot and mouth disease and swine vesicular disease. Consequently, outbreaks of vesicular stomatitis lead to rapid imposition of international quarantines and shutoff of trade of animals and animals products.

There is also public health concern because humans can be infected, Patterson, W. C., et al., J. Am. Vet. Med. Ass., 133, 57 (1958), and the virus may be spread by insect vectors, Ferris et al., J. Infect. Dis., 96, 184 (1955), Tesh et al., Science, 175, 1477 (1972).

VSV contains a single negative strand of ribonucleic acids (RNA), which encodes 5 messenger RNA's (mRNA's) and 5 known proteins, the nucleocapsid protein (N protein), the non-structural phosphoprotein (P protein or NS protein), the matrix protein (M protein), the G glycoprotein and the large polymerase protein (L protein). Two VSV serotypes, Indiana ($VSV_I$) and New Jersey ($VSV_{NJ}$), are known. Although the diseases caused by the two VSV serotypes are similar, they are immunologically distinct and are found in separate enzootic areas within the Western Hemisphere. Complementary desoxyribonucleic acids (DNA) copies of mRNA for the G, M, N, and NS proteins of $VSV_I$ have been cloned and sequenced (J. K. Rose et al., J. Virol., 39, 519 (1981); C. J. Gallione et al., J. Virol., 39, 529 (1981); C. J. Gallione et al., J. Virol., 46, 162 (1983). The G and N genes of the Indiana serotype have been expressed in eukaryotic cells (J. K. Rose et al., Cell, 30, 753 (1982); J. Sprague et al., J. Virol., 45, 773 (1983)). The sequence of the $VSV_{NJ}$ virus is reported in Gallione, C. J. and Rose, J. K., Journal of Virology 46, 162-169 (1983). This publication also reports the isolation of $VSV_{NJ}$ cDNA, including that corresponding to the genome segment, which encodes the G protein.

VSV are available before the American Type Culture Collection (ATCC), 12301 Parklawn Drive, Rockville, Md. 20852, USA. Notably, VSV of New Jersey serotype have been deposited at the ATCC under accession numbers No. VR-1239, and VR-159, and VSV of Indiana serotype under ATCC accession numbers No. VR-1238, VR-1415 to VR-1419 and VR-1421.

Nucleic acid sequences and amino acid sequences of the $VSV_{NJ}$ and $VSV_I$ have been published in various publications (i.e. Rose et al., Cell, 1980, 19(2): 415-421) and are also available in the NCBI database (i.e. accession numbers No. J02428, NC_001560).

Intranasal instillation of either serotype in mice can lead to lethal infections (Sabin and Olitsky, J. Exp. Med., 1937, 66: 15-34; Sabin and Olitsky, J. Exp. Med., 1938, 67: 201-227).

The only vaccine currently available for the control of vesicular stomatitis is an inactivated preparation (Bachmann et al., Med. Microbiol. Immunol., 1994, 183(2): 95-104; House et al., Vaccine, 2003, 21(17-18): 1932-1937). Use of this vaccine is restricted to states with confirmed cases of vesicular stomatitis or which are considered risky for incursion of the disease (Cantlon et al., Vaccine, 2000, 18: 2368-2374). Because this vaccine consists of whole virus, immunized animals are serologically indistinguishable from those that have been infected, and its widespread use is incompatible with effective surveillance of this disease. What is clearly needed for control of vesicular stomatitis is a vaccine that confers protective immunity, yet allows unambiguous differentiation of vaccinates from animals naturally infected with the viruses. Cantlon et al. (Cantlon et al., Vaccine, 2000, 18: 2368-2374) on the basis of plasmids, constructed in vivo expression vectors containing $VSV_{NJ}$ G gene under the control of the immediate early promoter from human cytomegalovirus. These plasmids were administered with immunostimulatory CpG-containing oligonucleotides and optionally with a plasmid expressing mouse interleukin-2 (mIL2) to mice in order to evaluate the immune response with respect to neutralizing antibody titer and mortality results. Neutralizing antibody titers were also observed on horses and cattle after plasmid administrations.

Mackett et al. (Mackett et al., Science, 1985, 227, 433-435) on the basis of the vaccinia virus, constructed in vivo expression vectors containing various inserts corresponding to nucleotide sequences encoding for proteins G of $VSV_{NJ}$ or G of $VSV_I$ or N of $VSV_I$. These recombinant viral vectors were administered to mice and cattle to evaluate the immune response with respect to neutralizing antibody titer and mortality results or clinical signs. The cattle vaccinated with recombinant vaccinia virus encoding G of $VSV_{NJ}$ developed significant VSV neutralization titers. However, all the cows developed lesions after $10^3$ PFU VSV challenge.

It would be advantageous to provide improved immunogenic and vaccine compositions against VSV, and methods for making and using such compositions, including such compositions that provide for differential diagnostic methods.

Citation or identification of any document in this application is not admission that such document is available as prior art to the present invention.

OBJECTS AND/OR SUMMARY OF THE INVENTION

The approach taken in this invention to VSV immunization is to produce a vaccine which may comprise a recombinant vector by inserting a polynucleotide sequence of the VSV viral genome into an in vivo expression vector that is non-pathogenic to the vaccinated animal so that a VSV peptide, polypeptide or protein is expressed by the recombinant vector. In a particular embodiment, a polynucleotide sequence of the VSV genome encoding a protein, a polypeptide or a peptide is inserted into a poxvirus genome, whereby the recombinant vector may function as a vaccine when inoculated into a VSV-susceptible animal.

In another particular embodiment, a polynucleotide sequence of the VSV genome encoding a protein, a polypeptide or a peptide may be inserted into a plasmid, whereby the plasmid may function as a vaccine when inoculated into a VSV-susceptible animal.

A first object of the present invention relates to a codon-optimized polynucleotide sequence encoding a VSV gene.

Another object relates to an in vivo expression vector comprising a polynucleotide sequence encoding a VSV gene, in particular a codon-optimized polynucleotide sequence encoding a VSV gene.

Still another object relates to a vaccine comprising a pharmaceutically or veterinary acceptable excipient, diluent or vehicle and/or an adjuvant and/or a stabilizer and at least one in vivo expression vector according to the present invention. The invention relates to immunogenic or vaccine compositions which may comprise at least one recombinant expression vector encoding at least one polypeptide of the invention, able to express in vivo this polypeptide in an animal. The invention therefore further relates to methods for preparing such vectors, e.g., inserting at least one polynucleotide encoding a polypeptide according to the invention into a plasmid vector or viral vector so that the vector expresses the polypeptide in the host. The invention therefore further relates to methods for formulating such immunogenic or vaccine compositions; e.g., admixing the vectors with a suitable veterinary or pharmaceutically acceptable excipient, diluent or vehicle and/or an adjuvant and/or stabilizer. The invention also relates to the use of such immunogenic or vaccine compositions; e.g., a method for eliciting an immunogenic response or a protective immune response, comprising administering the composition to an animal susceptible to VSV infection.

It is noted that in this disclosure and particularly in the claims, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF DRAWINGS

The following Detailed Description, given by way of example, and not intended to limit the invention to specific embodiments described, may be understood in conjunction with the accompanying Figures, incorporated herein by reference, in which:

FIG. 1 illustrates the nucleic acid sequence of the entire pJRL24 vector (SEQ ID NO: 14), having 6406 base pairs and comprising the left arm of the canarypox virus C5 gene [50-1585], the H6 promoter [1683-1806], the codon-optimized glycoprotein G gene of $VSV_{NJ}$ [1807-3360], the right arm of the canarypox virus C5 gene [3390-3794] and the ampicillin resistance gene. Amino acid sequence disclosed as SEQ ID NO: 15.

FIG. 2 illustrates the nucleic acid sequence of the entire pCXL1761.1 vector (SEQ ID NO: 16), having 6415 base pairs and comprising the left arm of the canarypox virus C5 gene [43-1578], the H6 promoter [1676-1799], the codon-optimized glycoprotein G gene of $VSV_I$ [1800-3332], the right arm of the canarypox virus C5 gene [3392-3796] and the ampicillin resistance gene. Amino acid sequence disclosed as SEQ ID NO: 16.

DETAILED DESCRIPTION OF THE INVENTION

Figure 3:
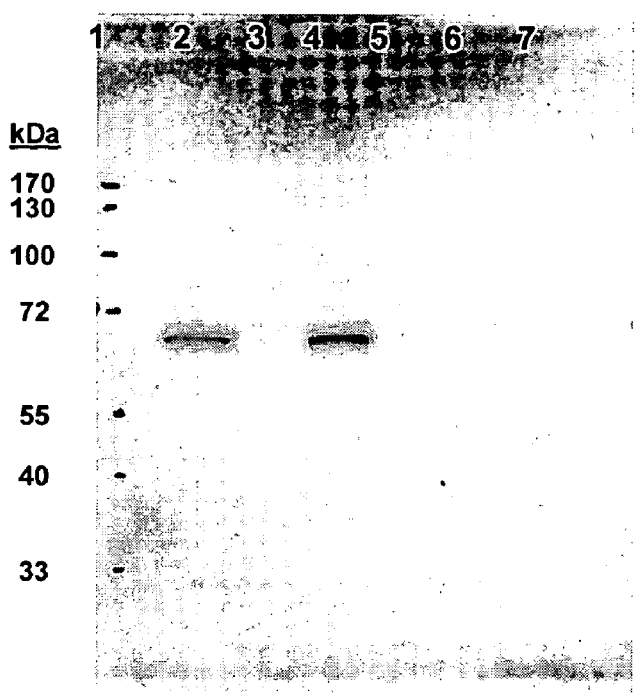
FIG. 3 presents Western blot analysis of primary chicken embryonic fibroblasts infected with vCP2300.

A first object of the present invention is a codon-optimized polynucleotide sequence encoding a VSV gene.

As starting material, VSV samples are available before the American Type Culture Collection (ATCC), 12301 Parklawn Drive, Rockville, Md. 20852, USA. In particular, VSV of New Jersey serotype have been deposited at the ATCC under accession numbers No. VR-1239, and VR-159, and VSV of Indiana serotype under ATCC accession numbers No. VR-1238, VR-1415 to VR-1419 and VR-1421. The genetic material of VSV can be extracted and purified by classical techniques. Reverse transcription polymerase chain reactions (RT-PCR) can be used to clone and to sequence cDNA fragment encoding a VSV gene (see Maniatis et al., Molecular Cloning: a Laboratory Manuel, Cold Spring Harbor Laboratory, 1982).

Codon preference among different species can be dramatically different. To enhance the expression level of a foreign protein, i.e. VSV G protein using a canarypox expression system (ALVAC) in a mammalian cell, it is very important to match the codon frequency of the foreign protein to the one of the host expression system (Kim et al., Gene, 1997, 199(1-2): 293-301). For codon optimization, other factors than codon frequency can be taken into consideration, e.g. DNA motifs and repeats, secondary structure, GC content, repetitive codons, restriction endonuclease sites, functional motifs like splice site or terminator structure. Algorithms have been created to facilitate the design of the optimal nucleotide sequence. Geneart GmbH (Regensburg, Germany) has developed the proprietary GeneOptimizer™ software (WO-A-04/059556 and WO-A-06/013103) that implements multi-parameter optimization in one single operation. Taking into account the most important parameters in parallel, the software generates a total of up to 500,000 optimized variants of the target sequence in an evolutionary approach and selects the one that is best suited. It has been reported that such optimized genes have up to a 100-fold increase in expression yields compared to the original gene sequence (Bradel-Tretheway et al., J. Virol. Methods, 2003, 111(2): 145-56; Disbrow et al., Virology, 2003, 311(1): 105-14).

The published nucleic acid sequences for G protein of VSV New Jersey serotype (NCBI accession AF170624; 1554 nucleotides; Llewellyn et al., Am. J. Vet. Res., 2000, 61(11): 1358-1363) and for G protein of VSV Indiana serotype (NCBI accession AF473864; 1536 nucleotides, starting from nucleotide 3078 to nucleotide 4613; Rodriguez et al., J. Gen. Virol., 2002, 83(10): 2475-2483) were optimized by the GeneOptimizer™ software.

The optimized synthetic nucleic acid sequence for G protein of $VSV_{NJ}$ is designated as SEQ ID NO: 1. The optimized and mutated synthetic nucleic acid sequence for G protein of $VSV_I$ is designated as SEQ ID NO: 7. These codon-optimized nucleic acid sequences encode a polypeptide having the same amino acid sequence that those disclosed in Llewellyn 2000 and in Rodriguez 2002. The codon-optimization changes only the nucleic acid sequence and not the encoded amino acid sequence.

Polynucleotides encoding other genes of VSV, notably N gene and M gene, can be codon-optimized, notably, as previously described for the G gene.

Polynucleotides according to the invention can be prepared in different ways (e.g. by chemical synthesis, by gene cloning etc.) and can take various forms (e.g. single stranded, double stranded, primers, probes etc.) (see Maniatis et al., Molecular Cloning: a Laboratory Manuel, Cold Spring Harbor Laboratory, 1982).

Polynucleotides according to the invention may be labeled e.g. with a radioactive or fluorescent label. This is particularly useful as a primer or as a probe.

In addition, the term "polynucleotide" includes DNA and RNA, and also their analogues, such as those containing modified backbones. It should be appreciated that the invention provides polynucleotides comprising sequences complementary to those described above.

The invention relates to in vivo expression vectors which contain at least one polynucleotide corresponding to sequences of the VSV viral genome encoding a polypeptide and which, when inoculated into a VSV-susceptible animal, induce an immune response, in particular induce an immune response able to protect against subsequent exposure to virulent VSV virus. Advantageously, this polynucleotide is codon-optimized.

The in vivo expression vectors of the present invention are recombinant poxviruses and recombinant polynucleotide vectors or plasmids (EP-A2-1001025; Chaudhuri P Res. Vet. Sci. 2001, 70(3), 255-6).

To produce the recombinant poxviruses, donor plasmids are prepared containing a poxvirus promoter, sites for insertion of the polynucleotide of interest and poxvirus flanking sequences. The polynucleotide of interest is a cDNA cloned from a VSV RNA genome or chemically synthetized. This polynucleotide encodes a VSV polypeptide according to the present invention. The polynucleotide can be codon-optimized as previously described. This polynucleotide is inserted in the donor plasmid under the control of a pox viral promoter and flanked by pox viral sequences. Cells are infected with a poxvirus, and the infected cells are transformed with the recombinant donor plasmids (Broder et al., Mol. Biotechnol., 1999, 13(3): 223-245; Carroll et al., Curr. Opin. Biotechnol., 1997, 8(5): 573-577). Homologous recombination of the donor plasmid DNA and the poxvirus DNA results in a recombinant poxvirus, which incorporate a VSV sequence.

The recombinant poxviruses according to the present invention can be a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO-A-96/40241), a swinepox virus, a capripox virus, a sheep-pox virus, a camelpox virus, an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807). Attenuated canarypox viruses are described in U.S. Pat. No. 5,756,103 (ALVAC) and WO-A-01/05934. Reference is also made to U.S. Pat. No. 5,766,599 which pertains to the attenuated fowlpox strain TROVAC. Reference is made to the canarypox available from the ATCC under access number VR-111. Reference is made to the fowlpox available from the ATCC under access number VR-229, VR-249, VR-250 and VR-251. Numerous fowlpox virus vaccinal strains are also available, e.g. the DIFTOSEC CT strain marketed by MERIAL and the NOBILIS VARIOLE vaccine marketed by INTERVET. Regarding the method to generate recombinants thereof and how to administer recombinants thereof, the skilled artisan can refer documents cited herein and to WO-A-90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and 5,766,599 inter alia; as to canarypox mention is made of U.S. Pat. No. 5,756,103 inter alia. When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters. Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter I3L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

Preferred constructs of recombinant poxvirus vectors according to the present invention are attenuated avipox viruses having, as insert, a polynucleotide encoding the G protein of VSV and/or the N protein of VSV and/or the M protein of VSV. In a particular embodiment, these attenuated avipox viruses are canarypox viruses, notably ALVAC. In another particular embodiment, recombinant poxvirus vectors according to the present invention are ALVAC viruses having, as insert, a codon-optimized polynucleotide encoding the G protein of VSV, i.e. vCP2300 and vCP2298 (see Examples 3 and 4, respectively).

Recombinant plasmids to express in vivo VSV immunogen(s), contain a polynucleotide encoding a VSV protein, polypeptide or peptide operably linked to a promoter. The polynucleotide of interest is a cDNA cloned from a VSV RNA genome or chemically synthetized. The polynucleotide can be codon-optimized as previously described.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention. In a specific, non-limiting example, the pVR1020 or pVR1012 plasmid (VICAL Inc.; Luke C. et al., Journal of Infectious Diseases, 1997, 175, 91-97; Hartikka J. et al., Human Gene Therapy, 1996, 7, 1205-1217) can be utilized as a vector for the insertion of a polynucleotide sequence. The pVR1020 plasmid is derived from pVR1012 and contains the human tPA signal sequence. Each plasmid comprises or contains or consists essentially of, in addition to the polynucleotide according to the present invention, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO-A-87/03905. The CMV-IE promoter is advantageously a human CMV-IE (Boshart M. et al., Cell, 1985, 41, 521-530) or murine CMV-IE. In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277). Functional sub fragments of these promoters, i.e., portions of these promoters that maintain an adequate promoting activity, are included within the present invention, e.g. truncated CMV-IE promoters according to PCT Application No. WO-A-98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156, 567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments. Advantageously, the plasmids comprise or consist essentially of other expression control elements. It is particularly advantageous to incorporate stabilizing sequence(s), e.g., intron sequence(s), preferably the first intron of the hCMV-IE (PCT Application No. WO-A-89/01036), the intron II of the rabbit β-globin gene (van Ooyen et al., Science, 1979, 206, 337-344). As to the polyadenylation signal (polyA) for the plasmids and viral vectors other than poxviruses, use can more be made of the poly(A) signal of the bovine growth hormone (bGH) gene (see U.S. Pat. No. 5,122, 458), or the poly(A) signal of the rabbit β-globin gene or the poly(A) signal of the SV40 virus.

Preferred constructs of recombinant plasmids according to the present invention are DNA plasmids having, as insert, a polynucleotide encoding the G protein of VSV and/or the N protein of VSV and/or the M protein of VSV. In a particular embodiment, these plasmids are pVR1012. In another particular embodiment, plasmids according to the present invention are pVR1012 having, as insert, a codon-optimized polynucleotide encoding the G protein of VSV; i.e. a recombinant pVR1012 plasmid with codon-optimized $VSV_{NJ}$ G gene having a nucleic acid sequence as SEQ ID NO: 1 under the control of CMV-IE promoter or a recombinant pVR1012 plasmid with codon-optimized $VSV_I$ G gene having a nucleic acid sequence as SEQ ID NO: 7 under the control of CMV-IE promoter.

Different in vivo expression vectors of the invention can further be associated in immunogenic or vaccine compositions; each vector having, as insert, a polynucleotide encoding the different protein of VSV or a protein of a different strain of VSV, notably selected among the group containing the G protein of $VSV_{NJ}$, the N protein of $VSV_{NJ}$, the M protein of $VSV_{NJ}$, the G protein of $VSV_I$, the N protein of $VSV_I$, the M protein of $VSV_I$.

The in vivo expression vectors of the invention can further be associated, in multivalent immunogenic or vaccine compositions, with at least another in vivo expression vector comprising at least one polynucleotide, advantageously encoding an immunogen, antigen or epitope from a pathogenic viral, parasitic, or bacterial agent, such viral agent is different from VSV, and/or with at least one inactivated viral, parasitic, or bacterial agent, such viral agent is different from VSV. For an equine multivalent immunogenic or vaccine composition, the viral, parasitic, or bacterial agents are advantageously chosen from among the group including: western equine encephalitis virus (WEEV), eastern equine encephalitis virus (EEEV), venezuelean equine encephalitis virus (VEEV), equine influenza virus, equine herpesvirus type 1 (EHV-1), equine herpesvirus type 4 (EHV-4), *Equine Artheritis* virus (EAV), West Nile virus (WNV), rabies virus, tetanus, *Streptococcus equi*. For a porcine multivalent immunogenic or vaccine composition, the viral, parasitic, or bacterial agents are advantageously chosen from among the group including, but not limited to: foot and mouth disease virus (FMDV), pseudorabies virus (PRV), porcine influenza virus, porcine parvovirus, porcine circovirus type 2 (PCV2), porcine reproductive and respiratory syndrome virus (PPRSV), *Mycoplasma hyopneumoniae*. For a bovine multivalent immunogenic or vaccine composition, the viral, parasitic, or bacterial agents are advantageously chosen from among the group including: bovine herpesvirus type 1 (BHV-1), bovine respiratory syncytial virus (BRSV), bovine viral diarrhea virus type 1 and type 2 (BVDV-1 and BVDV-2), type 3 parainfluenza virus, bovine rotavirus, bovine coronavirus, *Clostridium perfringens, Clostridium septicum, Clostridium tetani, Clostridium chauvoei, Clostridium novyi, Pasteurella multocida, Pasteurella haemolytica, Escherichia coli, Haemophilus somnus, Haemophilus pleuropneumoniae, Mycoplasma agalactiae, Mycoplasma bovis*.

By definition, an immunogen or antigen is a protein or polypeptide able to induce an immune response against the pathogenic agent, and contains one or more epitopes; an epitope is a peptide which is able to induce an immune response against the pathogenic agent.

The term "epitope" refers to the site on an antigen or hapten to which specific B cells and/or T cells respond. The term is also used interchangeably with "antigenic determinant" or "antigenic determinant site". Epitope determination procedures, such as, generating overlapping peptide libraries (Hemmer, B., C. Pinilla, et al. (1998). "The use of soluble synthetic peptide combinatorial libraries to determine antigen recognition of T cells." *J Pept Res* 52(5): 338-45), Pepscan (Geysen, H. M., R. H. Meloen, et al. (1984). "Use of peptide synthesis to probe viral antigens for epitopes to a resolution of a single amino acid." *Proc Natl Acad Sci USA* 81(13): 3998-4002); (Geysen, H. M., S. J. Barteling, et al. (1985). "Small peptides induce antibodies with a sequence and structural requirement for binding antigen comparable to antibodies raised against the native protein." *Proc Natl Acad Sci USA* 82(1): 178-82); (Van der Zee, R., W. Van Eden, et al. (1989). "Efficient mapping and characterization of a T cell epitope by the simultaneous synthesis of multiple peptides." *Eur J Immunol* 19(1): 43-7); (Geysen, H. M. (1990). "Molecular technology: peptide epitope mapping and the pin technology." *Southeast Asian J Trop Med Public Health* 21(4): 523-33); Multipin® Peptide Synthesis Kits of Chiron and algorithms (De Groot, A. S. and F. G. Rothman (1999). "In silico predictions; in vivo veritas." *Nat Biotechnol* 17(6): 533-4), can be used in the practice of the invention, without undue experimentation. Other documents cited and incorporated herein may also be consulted for methods for determining epitopes of an immunogen or antigen and thus nucleic acid molecules that encode such epitopes.

Another object of the invention is a recombinant immunogenic composition or vaccine comprising at least one recombinant in vivo expression vector according to the present invention, and a pharmaceutically acceptable excipient, diluent or vehicle, and optionally an adjuvant and/or a stabilizer.

The term "immunogenic composition" covers any composition that elicits an immune response against the targeted pathogen, notably that elicits a cytotoxic T cells response, and/or a secretory IgA response, and/or a systemic IgG response, in particular neutralizing antibodies; for instance, after administration or injection into the host, elicits an immune response against the targeted pathogen. The terms "vaccine" and "vaccine composition" cover any composition that induces a protective immune response against the targeted pathogen or which efficaciously protects against the pathogen; for instance, after administration or injection into the host, elicits a protective immune response against the targeted pathogen or provides efficacious protection against the pathogen. By definition, the protection induces a reduction of the clinical signs, i.e. vesicular lesions on the entire surface of the tongue, fever, damage to the tongue, death, and/or reduction of the local lesions, i.e. vesicular lesions at the challenge injection site.

The pharmaceutically or veterinary acceptable excipient, diluent or vehicle may be water, saline or buffer.

Examples of adjuvants are oil-in-water, water-in-oil-in-water emulsions based on mineral oil and/or vegetable oil and non ionic surfactants such as block copolymers, Tween®, Span®. Such emulsions are notably those described in page 147 of "Vaccine Design—The Subunit and Adjuvant Approach", Pharmaceutical Biotechnology, 1995, volume 6, edited by Michael F. Powell and Mark J. Newman, Plenum Press, New York and London, or TS emulsions, notably the TS6 emulsion, and LF emulsions, notably LF2 emulsion (for both TS and LF emulsions, see WO-A-04/024027). Other suitable adjuvants are for example vitamin E, saponins, and polymers of crosslinked acrylic or methacrylic acid, i.e. Carbopol® (Noveon; see WO-A-99/51269; WO-A-99/44633), Havlogen®, aluminium hydroxide or aluminium phosphate ("Vaccine Design, The subunit and adjuvant approach", Pharmaceutical Biotechnology, vol. 6, Edited by Michael F. Powell and Mark J. Newman, 1995, Plenum Press New York), biological adjuvants (i.e. C4b, notably murine C4b (Ogata R T et al., J. Biol. Chem. 1989, 264(28): 16565-16572) or equin C4b, GM-CSF, notably equine GM-CSF (U.S. Pat. No. 6,645,740)), toxins (i.e. cholera toxins CTA or CTB, *Escherichia coli* heat-labile toxins LTA or LTB . . . (Olsen C W et al., Vaccine, 1997, 15(10): 1149-1156; Fingerut E et al., Vaccine, 2005, 23(38): 4685-4696; Zurbriggen R et al., Expert Rev Vaccines, 2003, 2(2): 295-304; Peppoloni S et al., Expert Rev Vaccines, 2003, 2(2): 285-293)), and CpG (i.e. CpG #2395 (see Jurk M et al., Immunobiology 2004, 209(1-2): 141-154), CpG #2142 (see SEQ. ID. NO: 890 in EP-B1-1,221,955), CpG #2135, CpG #2007, CpG #2336). Polymers of crosslinked acrylic or methacrylic acid, especially crosslinked by polyalkenyl ethers of sugars or polyalcohols are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol® (Noveon) are especially suitable. They are crosslinked by allyl saccharose or by allyl pentaerythritol. Among them, reference is made to Carbopol 974P, 934P, 934, 940 and 971P.

The recombinant poxvirus immunogenic compositions and vaccines according to the invention may be freeze-dried advantageously with a stabiliser. Freeze-drying can be done according to well-known standard freeze-drying procedures. The pharmaceutically or veterinary acceptable stabilisers may be carbohydrates (e.g. sorbitol, mannitol, lactose, sucrose, glucose, dextran, trehalose), sodium glutamate (Tsvetkov T et al., Cryobiology 1983, 20(3): 318-23; Israeli E et al., Cryobiology 1993, 30(5): 519-23), proteins such as peptone, albumin, lactalbumin or casein, protein containing agents such as skimmed milk (Mills C K et al, Cryobiology 1988, 25(2): 148-52; Wolff E et al., Cryobiology 1990, 27(5): 569-75), and buffers (e.g. phosphate buffer, alkaline metal phosphate buffer). An adjuvant may be used to make soluble the freeze-dried preparations.

The invention further relates to methods for inducing in a VSV-susceptible animal, an immunogenic or protective immune response against VSV, comprising administering to the VSV-susceptible animal a recombinant immunogenic or vaccine composition of the invention.

By definition, VSV-susceptible animals encompasse bovine (i.e. cattle, cows, calves), equine (i.e. horses, mares, foals, ponies, donkeys and mules), porcine (i.e. pigs, sows, piglets), ovine (i.e. sheep), caprine (i.e. goats) and human. These animals are also the preferred hosts for administration of the vaccine according to the present invention.

According to these methods, (1) a recombinant poxvirus immunogenic composition or vaccine of the present invention, or (2) a recombinant plasmid immunogenic composition or vaccine of the present invention, or their combinations, are administered. In one embodiment of the invention, the recombinant vectors can be used in a prime-boost regimen, such as where a vaccine or immunogenic composition of the invention is administered first, a different vaccine or immunogenic composition is administered thereafter, with the proviso that first and second vaccine or immunogenic compositions have at least one immunogen in common. Particular prime-boost regimen can be that a recombinant plasmid vaccine or immunogenic composition of the invention is administered first and a recombinant poxvirus vaccine or immunogenic composition of the invention is administered thereafter. Another particular prime-boost regimen can be that a recombinant plasmid vaccine or immunogenic composition of the invention is administered first and an inactivated VSV vaccine or immunogenic composition of the invention is administered thereafter.

The administration may be notably made by intramuscular (IM), intradermal (ID), subcutaneous (SC) or transdermal injection or via intranasal, intratracheal, oral administration. The immunogenic composition or the vaccine according to the invention is administered by syringe, a syringe with a microneedle (i.e. BD™ Intradermal Delivery System of Becton, Dickinson and Company, Franklin Lakes, N.J., USA), needlefree apparatus (like for example Pigjet, Avijet, Dermojet or Biojector (Bioject, Oreg., USA), see US-A-2006/0034867) or a spray. The route of administration is preferrably by IM injection with a syringe, or by transdermal injection with a needlefree apparatus or with a syringe with a microneedle (i.e. BD™ Intradermal Delivery System), or by intranasal or oral administration with a spray, i.e. a liquid nebulisation of a vaccine of the invention, or by oral or nasal administration of a micronized powder of a freeze-dried vaccine according to the invention.

The quantity of recombinant vector in the immunogenic compositions or vaccines can be determined and optimised by the skilled person, without undue experimentation from this disclosure and the knowledge in the art. Generally an animal (including a human) may be administered approximately $10^4$-$10^9$ CFU, advantageously approximately $10^5$-$10^8$ CFU and more advantageously approximately $10^6$-$10^8$ CFU in a single dosage unit of recombinant viral immunogenic compositions or vaccines of the present invention; approximately 10 ng-1 mg, advantageously approximately 100 ng-500 µg and more advantageously approximately 1 µng-250 µg per plasmid type in a single dosage unit of recombinant DNA immunogenic compositions or vaccines of the present invention.

The volume of one single dosage unit by syringe can be between about 0.2 ml and about 5.0 ml and advantageously between about 0.5 ml and about 2.0 ml and more advantageously about 1.0 ml. The volume of one single dosage unit by needlefree apparatus can be between about 0.1 ml and about 1.0 ml and advantageously between about 0.2 ml and about 0.5 ml. The volume of one single dosage unit by liquid spray can be between about 2.0 ml and about 10.0 ml and advantageously about 5.0 ml (for powder spray, the quantities administered are corresponding to the equivalent volumes).

A vaccine based on plasmid or a viral vector expressing one or more proteins of the VSV according to the present invention will not induce in the immunized or vaccinated animal antibodies against other proteins of the virus, which are not presented in or by the immunogenic composition or vaccine (e.g., not present in the immunogenic composition or vaccine and/or not expressed by the immunogenic composition or vaccine). By this feature, the instant invention provides differential diagnostic methods. The present invention makes possible a distinction between animals infected by the vesicular stomatitis pathogenic virus and animals vaccinated or immunized with vaccines or compositions according to the invention. In order to bring about this distinction, the diagnostic method employs a protein which is not represented in or by the vaccine or immunogenic composition (not present and/or not expressed), e.g. protein NS or protein L, or protein G, N, or M when not represented in the vaccine or immunogenic composition according to the invention.

The invention will now be further described by way of the following non-limiting examples.

Constructions of cDNA inserts, plasmids, recombinant poxviruses were carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989). All the restriction fragments used for the present invention were isolated using the "Geneclean" kit (BIO 101 Inc., La Jolla, Calif.).

Example 1

Construction of Donor Plasmid pJRL24 Containing Codon-Optimized Glycoprotein G gene of $VSV_{NJ}$ The nucleic acid sequence for G protein of VSV New Jersey serotype (NCBI accession AF170624; 1554 nucleotides) was codon-optimized by Geneart GmbH (Regensburg, Germany) using the GeneOptimizer™ software.

The optimized synthetic nucleic acid sequence for G protein of $VSV_{NJ}$ was designated as SEQ ID NO: 1 (1554 mer):

```
5'ATGCTGTCCTACCTGATCCTGGCCATCATCGTGTCCCCTATCCTGGGCAAGATCGAGATC

GTGTTCCCCCAGCACACCACCGGCGATTGGAAGAGAGTGCCCCACGAGTACAACTACTGCCC

TACCAGCGCCGACAAGAATAGCCACGGCACCCAGACCGGCATCCCCGTGGAGCTGACCATGC

CCAAGGGCCTGACCACCCACCAGGTGGACGGCTTCATGTGCCACAGCGCCCTGTGGATGACC

ACCTGTGACTTCAGATGGTACGGCCCCAAGTACATCACCCACAGCATCCACAACGAGGAGCC

CACCGATTACCAGTGCCTGGAGGCCATCAAGGCCTACAAGGACGGAGTGGGCTTCAATCCTG

GCTTCCCCCCCAGAGCTGTGGCTACGGCACCGTGACCGACGCCGAGGCCCACATCATCACC

GTGACCCCCCACAGCGTGAAGGTGGACGAGTACACCGGCGAGTGGATCGACCCCCACTTCAT

CGGCGGCAGGTGTAAGGGCAAAATCTGTGAGACCGTGCACAACAGCACCAAGTGGTTCACCA

GCAGCGACGGCGAGAGCGTGTGTAGCCAGCTGTTCACCCTGGTGGGCGGCACCTTCTTCAGC

GACAGCGAGGAGATCACCAGCATGGGCCTGCCCGAGACAGGCATCCGGAGCAACTACTTCCC
```

-continued

```
CTACATCAGCACCGAGGGCATCTGTAAGATGCCATTTTGCCGGAAGCCTGGCTACAAGCTGA

AGAACGACCTGTGGTTCCAGATCACCGACCCCGACCTGGACAAGACAGTGAGAGACCTGCCC

CACATCAAGGACTGTGACCTGAGCAGCAGCATCATCACCCCTGGCGAGCACGCCACCGATAT

CAGCCTGATCAGCGACGTGGAGCGGATCCTGGACTACGCCCTGTGCCAGAATACCTGGGGGA

AGATCGAGGCCGGCGAGCCCATCACCCCCGTGGACCTGAGCTACCTGGGCCCTAAGAATCCC

GGAGTGGGCCCTGTGTTCACCATCATCAACAGCAGCCTGCACTACTTCACCAGCAAGTACCT

GAGGGTGGAGCTGGAGAGCCCTGTGATCCCTAGGATGGAGGGCAGAGTGGCCGGCACCAGGA

TTGTGAGACAGCTGTGGGACCAGTGGTTCCCCTTCGGCGAGGCCGAGATCGGCCCCAACGGC

GTGCTGAAAACCAAGCAGGGCTACAAGTTCCCCCTGCACATCATCGGCACAGGCGAGGTGGA

CAGCGACATCAAGATGGAGAGGATCGTGAAGCACTGGGAGCACCCTCACATCGAGGCCGCCC

AGACCTACCTGAAGAAGGACGACACCGAGGAGGTGATCTACTACGGCGACACCGGCATCAGC

AAGAACCCTGTGGAACTGGTGGAGGGCTGGTTCAGCGGCTGGAGGAGCAGCATTATGGGCGT

GGTGGCCGTGATCATCGGCTTCGTGATCCTGATCTTCCTGATCCGGCTGATCGGCGTGCTGT

CCACCCTGTTCCGGCCTAAGCGGAGGCCTATCTACAAGTCCGACGTGGAGATGGCCCACTTC

CGGTGA 3'.
```

This sequence was amplified by PCR using PCR primers, 13303.JL and 13304.JL, generating a PCR product of 1608 base pairs (bp).

13303.JL was designated as SEQ ID NO: 2 (64 mer):

```
5'TATCCTTGTCGCGATATCCGTTAAGTTTGTATCGTAATGCTGTCCTACCTGATCCTGGCC

ATCA 3'
``` and 13304.JL as SEQ ID NO: 3 (30 mer):

```
5'AACTAGTCATAAAAATCATCACCGGAAGTG 3'.
```

The 13303.JL primer introduced an Nru I site and a fragment of the H6 promoter including its 3'-end. The 13304.JL primer introduced an Spe I site. The insert DNA was generated by sequential restriction of this PCR product with Spe I and Nru I. Vector DNA was prepared by sequential restriction of the plasmid pCXL148.2 with Spe I followed by Nru I. These restrictions excised from the vector the equivalent H6 promoter fragment of that contained in the insert DNA. T4 DNA ligase was used to clone the 1591 bp insert DNA into the vector DNA. In this way, the codon-optimized glycoprotein G gene of $VSV_{NJ}$ was cloned into pCXL148.2 under the control of the thusly-restored H6 promoter and between the left and right recombination arms of the canarypox virus C5 gene. The resulting plasmid was designated pJRL24, whose entire nucleic acid sequence is given in FIG. 1.

Example 2

Construction of Donor Plasmid pCXL1761.1 Containing Codon-Optimized Glycoprotein G Gene of $VSV_I$ The nucleic acid sequence for G protein of VSV Indiana serotype (NCBI accession AF473864; 1536 nucleotides, starting from nucleotide 3078 to nucleotide 4613) was codon-optimized by Geneart GmbH (Regensburg, Germany) using the GeneOptimizer™ software.

The optimized synthetic nucleic acid sequence for G protein of $VSV_I$ was designated as SEQ ID NO: 4 (1560 mer):

```
5'GTCGACGCCGCCACCATGAAGTGCCTGCTGTACCTGGCCTTCCTGAGCATCGGCGTGAAC

TGCAAGTTCACCATCGTGTTCCCCCACAACCAGAAGGGCACCTGGAAGAACGTGCCCAGCAA

CTACCACTACTGCCCCAGCAGCAGCGATCTGAACTGGCACAACGACCTGATCGGCACCGCCC

TGCAGGTGAAGATGCCCAAGAGCCACAAGGCCATCCAGGCCGACGGCTGGATGTGCCACGCC

AGCAAGTGGGTGACCACCTGCGACTTCAGATGGTACGGCCCCAAGTACATCACCCACAGCAT

CAGGAGCTTCACCCCTAGCGTGGAGCAGTGCAGGGAGAGCATCGAGCAGACCAAGCAGGGCA

CATGGCTGAATCCTGGCTTCCCTCCCCAGAGCTGCGGCTACGCCACCGTGACCGACGCCGAG
```

```
                      -continued
GCCGTGATCGTGCAGGTGACCCCCCACCACGTGCTGGTCGATGAGTACACCCGCGAGTGGGT

GGACAGCCAGTTCATCAACGGCAAGTGCAGCAACGACATCTGCCCCACCGTGCACAACAGCA

CCACCTGGCACAGCGACTACAAAGTGAAGGGCCTGTGCGACAGCAACCTGATCAGCATGGAC

ATCACCTTTTTCAGCGAGGACGGCGAGCTGAGCAGCCTGGGCAAGGAGGGCACCGGCTTCAG

AAGCAACCACTTCGCCTACGAGACCGGCGACAAGGCCTGCAAGATGCAGTACTGCAAGCACT

GGGGAGTGAGACTGCCCAGCGGCGTGTGGTTCGAGATGGCCGACCAGGACCTGTTCGCCGCC

GCCAGATTCCCCGAGTGCCCCGAGGGCAGCAGCATCAGCGCCCCCAGCCAGACCAGCGTGGA

TGTGAGCCTGATCCAGGACGTGGAGCGGATCCTGGATTACAGCCTGTGCCAGGAGACCTGGA

GCAAGATCGGAGCCGGCCTGCCCATCAGCCCCGTGGACCTGAGCTACCTGGCCCCTAAGAAC

CCCGGCACCGGCCCAGCCTTCACCATCATCAACGGGACCCTGAAGTACTTCGAGACCCGGTA

CATCAGAGTGGACATTGCCGCCCCTATCCTGAGCAGAATGGTGGGCATGATCAGCGGCACCA

CCACCGAGAGAGCTGTGGGACGATTGGGCCCCTTACGAGGATGTGGAGATCGGCCCTAAC

GGCGTGCTGAGAACCAGCAGCGGCTACAAGTTCCCCCTGTACATGATCGGCCACGGCATGCT

GGACAGCGACCTGCACCTGAGCAGCAAGGCCCAGGTGTTCGAGCACCCCCACATCCAGGACG

CCGCCAGCCAGCTGCCCGACGACGAGACCCTGTTCTTCGGCGACACCGGCCTGAGCAAGAAC

CCTATCGAACTGGTGGAGGGCTGGTTCAGCGGCTGGAAGAGCAGCATCGCCAGCTTTTTCTT

CATCATCGGCCTGATCATCGGGCTGTTTCTGGTGCTGAGAGTGGGCATCTACCTGTGCATCA

AGCTGAAGCACACCAAGAAGCGGCAAATCTACACCGACATCGAGATGAACCGGCTGGGCAAG

TGATGAAGATCT 3'.
```

This sequence has a T5CT motif in its 3' end. This motif has been changed to TTCTTCT using Stratagene's QuikChange Site-directed Mutagenesis Kit (Cat#200518), with two overlapping primers 13299.CXL and 13300.CXL. The plasmid pCXL1734.1 was one of the three mutated plasmid obtained.

13299.CXL was designated as SEQ ID NO: 5 (33 mer):

```
5' GCAGCATCGCCAGCTTCTTCTTCATCATCGGCC 3'
``` and 13300.CXL as SEQ ID NO: 6 (33 mer):

```
5' GGCCGATGATGAAGAAGAAGCTGGCGATGCTGC 3'.
```

The optimized and mutated synthetic nucleic acid sequence for G protein of VSV$_I$ was designated as SEQ ID NO: 7 (1536 mer):

```
5'ATGAAGTGCCTGCTGTACCTGGCCTTCCTGAGCATCGGCGTGAACTGCAAGTTCACCATC

GTGTTCCCCCACAACCAGAAGGGCACCTGGAAGAACGTGCCCAGCAACTACCACTACTGCCC

CAGCAGCAGCGATCTGAACTGGCACAACGACCTGATCGGCACCGCCCTGCAGGTGAAGATGC

CCAAGAGCCACAAGGCCATCCAGGCCGACGGCTGGATGTGCCACGCCAGCAAGTGGGTGACC

ACCTGCGACTTCAGATGGTACGGCCCCAAGTACATCACCCACAGCATCAGGAGCTTCACCCC

TAGCGTGGAGCAGTGCAGGGAGAGCATCGAGCAGACCAAGCAGGGCACATGGCTGAATCCTG

GCTTCCCTCCCCAGAGCTGCGGCTACGCCACCCTGACCGACGCCGAGGCCGTGATCGTGCAG

GTGACCCCCCACCACGTGCTGGTCGATGAGTACACCGGCGAGTGGGTGGACAGCCAGTTCAT

CAACGGCAAGTGCAGCAACGACATCTGCCCCACCGTGCACAACAGCACCACCTGGCACAGCG

ACTACAAAGTGAAGGGCCTGTGCGACAGCAACCTGATCAGCATGGACATCACCTTTTTCAGC

GAGGACGGCGAGCTGAGCAGCCTGGGCAAGGAGGGCACCGGCTTCAGAAGCAACCACTTCGC

CTACGAGACCGGCGACAAGGCCTGCAAGATGCAGTACTGCAAGCACTGGGGAGTGAGACTGC

CCAGCGGCGTGTGGTTCGAGATGGCCGACCAGGACCTGTTCGCCGCCGCCAGATTCCCCGAG

TGCCCCGAGGGCAGCAGCATCAGCGCCCCCAGCCAGACCAGCGTGGATGTGAGCCTGATCCA
```

-continued
```
GGACGTGGAGCGGATCCTGGATTACAGCCTGTGCCAGGAGACCTGGAGCAAGATCGGAGCCG

GCCTGCCCATCAGCCCCGTGGACCTGAGCTACCTGGCCCCTAAGAACCCCGGCACCGGCCCA

GCCTTCACCATCATCAACGGGACCCTGAAGTACTTCGAGACCCGGTACATCAGAGTGGACAT

TGCCGCCCCTATCCTGAGCAGAATGGTGGGCATGATCAGCGGCACCACCACCGAGAGAGAGC

TGTGGGACGATTGGGCCCCTTACGAGGATGTGGAGATCGGCCCTAACGGCGTGCTGAGAACC

AGCAGCGGCTACAAGTTCCCCCTGTACATGATCGGCCACGGCATGCTGGACAGCGACCTGCA

CCTGAGCAGCAAGGCCCAGGTGTTCGAGCACCCCACATCCAGGACGCCGCCAGCCAGCTGC

CCGACGACGAGACCCTGTTCTTCGGCGACACCGGCCTGAGCAAGAACCCTATCGAACTGGTG

GAGCGCTGGTTCAGCGGCTGGAAGAGCAGCATCGCCAGCTTCTTCTTCATCATCGGCCTGAT

CATCGGGCTGTTTCTGGTGCTGAGAGTGGGCATCTACCTGTGCATCAAGCTGAAGCACACCA

AGAAGCGGCAAATCTACACCGACATCGAGATGAACCGGCTGGGCAAGTGA 3'.
```

This mutated sequence was amplified by PCR using pCXL1734.1 as template, and PCR primers, 13289CXL and 13290CXL. A PCR product of 1580 bp was generated.

13289CXL was designated as SEQ ID NO: 8 (52 mer):

```
5' CGCGATATCCGTTAAGTTTGTATCGTAATGAAGTGCCTGCTGTACCTGGCCT 3'
``` and 13290CXL as SEQ ID NO: 9 (38 mer):

```
5' CTAGACTCGAGCTATCATCACTTGCCCAGCCGGTTCAT 3'.
```

The 13289CXL primer introduced an EcoRV site and a fragment of the H6 promoter including its 3'-end. The 13290CXL primer introduced an Xho I site. The insert DNA was generated by sequential restriction of this PCR product with Xho I and EcoRV. Vector DNA was prepared by sequential restriction of the plasmid pCXL148.2 with Xho I followed by EcoRV. These restrictions excised from the vector the equivalent H6 promoter fragment of that contained in the insert DNA. T4 DNA ligase was used to clone the 1564 bp insert DNA into the vector DNA. In this way, the codon-optimized glycoprotein G gene of $VSV_I$ was cloned into pCXL148.2 under the control of the thusly-restored H6 promoter and between the left and right recombination arms of the canarypox virus C5 gene. The resulting plasmid was designated pCXL1761.1, whose entire nucleic acid sequence is given in FIG. 2.

Example 3

Construction of Canarypox Virus Recombinant vCP2300 expressing the codon-optimized glycoprotein G gene of $VSV_{NJ}$ The in vitro recombination was performed by transfection of primary chicken embryo fibroblast cells (CEF cells) with of 15 μg Not I-linearized donor plasmid pJRL24 (see example 1) using FUGENE-6® transfection reagent (Roche). The primary CEF cells grown in 10% FBS (HyClone: gamma-irradiated Fetal bovine serum certified Australinan, Cat# SV30015.04), DMEM (BRL/Gibco#11960-051 or 11960-044) supplemented with 4 mM Glutamine (BRL/Gibco#25030-081) and 1 mM Sodium Pyruvate (BRL/Gibco#11360-070) in the presence of 1× antibiotics/antimycotics (P/S/A/A, BRL/Gibco#15240-062). The transfected cells were subsequently infected with the rescue canarypox virus, ALVAC ($6.3 \times 10^9$ pfu/ml), at a multiplicity of infection (MOI) of 10. Twenty-four hours post-infection the cells were harvested and sonicated. The ensuing lysate was screened for recombinant virus.

Recombinant plaques were screened by plaque hybridization using a 669 bp DNA probe specific for synthetic, codon-optimized G (G-specific probe) which was labeled with horseradish peroxidase according to the manufacturer's protocol (Amersham Cat# RPN3001). The G-specific probe has been produced by PCR amplification using primers 13305.JL and 13308.JL, and pJRL24 as template.

13305.JL was designated as SEQ ID NO: 10 (19 mer):

```
5' CCCACATCATCACCGTGAC 3'
``` and 13308.JL as SEQ ID NO: 11 (21 mer):

```
5' TCCTAGGGATCACAGGGCTCT 3'.
```

After three sequential rounds of plaque purification, the recombinant designated as vCP2300 was isolated and confirmed by plaque hybridization assay to be positive for G and without detectable parental virus.

A single plaque was selected from the fourth round of plaque purification, and expanded to obtain stocks of vCP2300. Concentration of virus from the monolayers of five roller bottles yielded ~4.00 mL at $7.85 \times 10^9$ pfu/mL.

Genomic DNA from vCP2300 was extracted and restricted in parallel with BamH I, Hind III or Pst I. The restriction fragments were separated on a 0.8% agarose gel. The best indications yielded by restriction analysis that G had been inserted into the C5 loci were the elimination of restriction fragments (Hind III-10485 bp and Pst I-17675 bp) specific to the parental virus from the recombinant samples.

The expression of the insert was analyzed.

Primary CEF cells were infected with vCP2300 at MOI of 157 and incubated for 24 hours. Cell lysates and supernatant samples were prepared and their constituent proteins separated by PAGE on a 10% Bis-Tris gel under reducing conditions. The proteins were transferred to an Invitrolon PVDF membrane. An approximately 67 kDa band was detected 30 in vCP2300-infected cell lysates using rabbit anti-$VSV_{NJ}$ (Ogden) serum (see FIG. 3). This band was absent from vCP2300 supernatant and both parental ALVAC-infected samples. While larger than predicted (58.3 kDa for the unmodified peptide), this band appears to be G. The apparent increase in size may be a result of glycosylation or may be an artifact of the electrophoresis system.

Example 4

Construction of Canarypox Virus Recombinant Expressing the Codon-Optimized Glycoprotein G Gene of $VSV_I$ The in vitro recombination was performed by transfection of primary CEF cells with of 18 µg Not I-linearized donor plasmid pCXL1761.1 (see example 2) using FUGENE-6® transfection reagent (Roche). The primary CEF cells grown as described in example 3. The transfected cells were subsequently infected with the rescue canarypox virus, ALVAC ($6.3 \times 10^9$ pfu/ml), at a MOI of 10. Twenty-four hours post-infection the cells were harvested and sonicated. The ensuing lysate was screened for recombinant virus.

Recombinant plaques were screened by plaque lift hybridization using a 1202 bp DNA probe specific for synthetic, codon-optimized G (G-specific probe) which was labeled with horseradish peroxidase according to the manufacturer's protocol (Amersham Cat# RPN3001). The G-specific probe has been produced by PCR amplification using primers 13289CXL and 13294CXL, and pCXL1761.1 as template.

13289CXL was designated as SEQ ID NO: 12 (52 mer):

5' CGCGATATCCGTTAAGTTTGTATCGTAATGAAGTGCCTGCTGTACCTGGCCT 3' and 13294CXL as SEQ ID NO: 13 (24 mer):

5' GCTGCTGGTTCTCAGCACGCCCTT 3'.

After four sequential rounds of plaque purification, the recombinant designated as vCP2298 was generated and confirmed by hybridization as 100% positive for the G insert and 100% negative for the empty C5 site.

A single plaque was selected from the fourth round of plaque purification, and expanded to obtain stocks to amplify vCP2298. The infected cell culture fluid from the roller bottles was harvested and concentrated to produce the virus stock. Final virus concentrates were resuspended in 1 mM Tris, pH9.0, and the titres were $1.83 \times 10^9$ pfu/ml in 2.5 ml.

Genomic DNA from vCP2298 was extracted and restricted in parallel with BamH I, Hind III or Pst I. The restriction fragments were separated on a 0.8% agarose gel. The results revealed the correct insertion of VSV synthetic G sequence.

The expression of the insert was analyzed.

Figure 4:
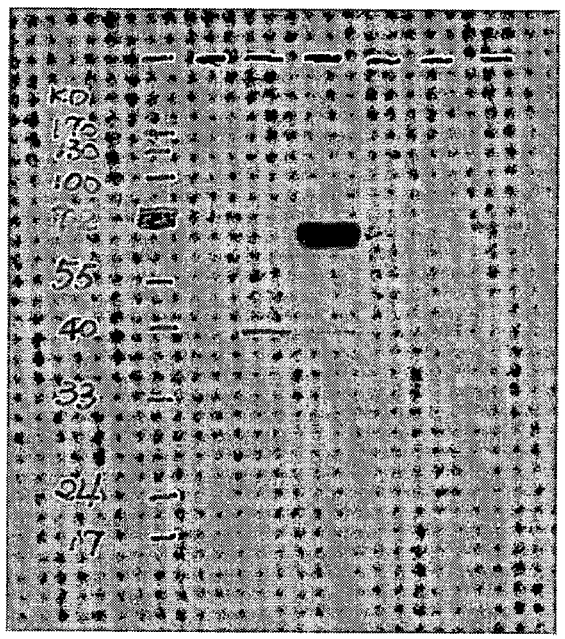
FIG. 4 presents Western blot analysis of primary chicken embryonic fibroblasts infected with vCP2298.

Primary CEF cells were infected with vCP2298 at MOI of 10 and incubated at 37° C. for 25 hours. The cells and culture supernatant were then harvested. Sample proteins were separated on a 10% SDS-PAGE gel, transferred to Invitrolon PVDF membrane, and probed with rabbit anti-VSV G polyclonal antibody (IGL#RVV-65A-2 at 1 in 200 dilution). Peroxidase-conjugated Goat anti-rabbit antiserum was used as a secondary antibody and the bands were visualized using luminol reagents. vCP2298 showed a very strong band at about 65 kDa in the cell pellet fraction, and much weak band in the culture supernatant fraction (see FIG. 4).

Example 5

Evaluation of VSV Vaccines in Mice

Seven groups of outbreak ICR mice, purchased at 4-6 weeks of age are used. The mice are immunized twice 3 weeks apart according to the following schedule. Vaccines will be administered by subcutaneous injection.

| Group | Vaccine | Dose (log10 TCID50) |
| --- | --- | --- |
| 1 | VS-NJ | 7 |
| 2 | VS-NJ | 6 |
| 3 | VS-NJ | 5 |
| 4 | VS-IN | 7 |
| 5 | VS-IN | 6 |
| 6 | VS-IN | 5 |
| 7 | None | — |

Blood is collected on day 0, 21, and 35 and serum stored for neutralization assay. The assay is a microneutralization assay recommended by the National Veterinary Services Lab, and the challenge virus reflects the serotype of the vaccine given to each mouse (i.e. mice immunized with VS-NJ is only tested for antibodies against VS-NJ; controls are tested for antibodies to both serotypes).

On day 35 (two weeks after the second dose of vaccine) all mice are challenged by intranasal administration of homologous VS virus; five control mice are challenged with VS-NJ and five with VS-IN. Challenged mice are monitored for morbidity and mortality over a 14 day period.

Example 6

Evaluation of VSV Vaccines in Horses

Twenty (20) horses (males and/or females) from 6 months of age are randomly assigned to one of two groups (A and B) of 10 horses. The horses from group A are vaccinated 4-6 weeks apart with one dose (1-2 mL) of vCP2300 (New Jersey) or vCP2298 (Indiana). Horses from group B are not vaccinated and serve as controls for the challenge. The vaccines contain 10E5-10E8 TCID50 of canarypox virus per dose in the presence of 4 to 6 mg of Carbopol 974. Vaccines are administered by deep intramuscular injection in the neck or pectoral muscles.

Blood is collected on day 0 (prior to V1), 7, 14, 35 (prior to V2), 49 (prior to challenge) and 63 and serum stored for neutralization assay. The assay is a microneutralization assay recommended by the National Veterinary Services Lab, and the challenge virus reflects the serotype of the vaccine given to the horses (i.e. horses immunized with VS-NJ is only tested for antibodies against VS-NJ).

On day 49 (two weeks after the second dose of vaccine) all horses are challenged by injection of homologous VS virus in the tongue epithelium. Challenged horses are monitored for general condition, fever and tongue lesions over a 14-day period.

What is claimed is:

1. A nucleic acid molecule comprising the sequence of SEQ ID NO: 7.

2. A nucleic acid molecule comprising the sequence of SEQ ID NO: 1.

3. An in vivo poxvirus expression vector, that contains and expresses in vivo, the nucleic acid molecule of claim 1 or 2.

4. An immunogenic composition for inducing an immune response against VSV in a VSV-susceptible animal, which comprises the recombinant in vivo expression vector according to claim 3.

5. The composition comprising the poxvirus expression vector of claim 3 wherein the poxvirus is an avipox virus.

6. The composition according to claim 5 wherein the avipoxvirus is a canarypox virus.

7. The composition according to claim 6 wherein the canarypox virus is ALVAC.

8. An immunogenic composition comprising recombinant poxvirus, wherein the recombinant poxvirus comprises the plasmid having the sequence as set forth in SEQ ID NO:16.

9. An immunogenic composition comprising recombinant poxvirus, wherein the recombinant poxvirus comprises the plasmid having the sequence as set forth in SEQ ID NO:14.

* * * * *

SEQUENCE LISTING

<160> NUMBER OF SEQ ID NOS: 17

<210> SEQ ID NO 1
<211> LENGTH: 1554
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1

| | | |
|---|---|---|
| atgctgtcct acctgatcct ggccatcatc gtgtccccta tcctgggcaa gatcgagatc | 60 |
| gtgttccccc agcacaccac cggcgattgg aagagagtgc cccacgagta caactactgc | 120 |
| cctaccagcg ccgacaagaa tagccacggc acccagaccg gcatcccgt ggagctgacc | 180 |
| atgcccaagg gcctgaccac ccaccaggtg gacggcttca tgtgccacag cgccctgtgg | 240 |
| atgaccacct gtgacttcag atggtacggc cccaagtaca tcacccacag catccacaac | 300 |
| gaggagccca ccgattacca gtgcctggag gccatcaagg cctacaagga cggagtgggc | 360 |
| ttcaatcctg gcttcccccc ccagagctgt ggctacggca ccgtgaccga cgccgaggcc | 420 |
| cacatcatca ccgtgacccc ccacagcgtg aaggtggacg agtacaccgg cgagtggatc | 480 |
| gacccccact tcatcggcgg caggtgtaag ggcaaaatct gtgagaccgt gcacaacagc | 540 |
| accaagtggt tcaccagcag cgacggcgag agcgtgtgta gccagctgtt caccctggtg | 600 |
| ggcggcacct tcttcagcga cagcgaggag atcaccagca tgggcctgcc cgagacaggc | 660 |
| atccggagca actacttccc ctacatcagc accgagggca tctgtaagat gccattttgc | 720 |
| cggaagcctg gctacaagct gaagaacgac ctgtggttcc agatcaccga ccccgacctg | 780 |
| gacaagacag tgagagacct gccccacatc aaggactgtg acctgagcag cagcatcatc | 840 |
| acccctggcg agcacgccac cgatatcagc ctgatcagcg acgtggagcg gatcctggac | 900 |
| tacgccctgt gccagaatac ctgggggaag atcgaggccg cgagcccat cacccccgtg | 960 |
| gacctgagct acctgggccc taagaatccc ggagtgggcc ctgtgttcac catcatcaac | 1020 |
| agcagcctgc actacttcac cagcaagtac ctgagggtgg agctggagag ccctgtgatc | 1080 |
| cctaggatgg agggcagagt ggccggcacc aggattgtga cagctgtg gaccagtgg | 1140 |
| ttccccttcg gcgaggccga gatcggcccc aacggcgtgc tgaaaaccaa gcagggctac | 1200 |
| aagttccccc tgcacatcat cggcacaggc gaggtggaca gcgacatcaa gatggagagg | 1260 |
| atcgtgaagc actgggagca ccctcacatc gaggccgccc agacctacct gaagaaggac | 1320 |
| gacaccgagg aggtgatcta ctacggcgac accggcatca gcaagaaccc tgtggaactg | 1380 |
| gtggagggct ggttcagcgg ctggaggagc agcattatgg gcgtggtggc cgtgatcatc | 1440 |
| ggcttcgtga tcctgatctt cctgatccgg ctgatcggcg tgctgtccag cctgttccgg | 1500 |
| cctaagcgga ggcctatcta caagtccgac gtggagatgg cccacttccg gtga | 1554 |

<210> SEQ ID NO 2
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tatccttgtc gcgatatccg ttaagtttgt atcgtaatgc tgtcctacct gatcctggcc    60

```
atca                                                                64
```

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
aactagtcat aaaaatcatc accggaagtg                                    30
```

<210> SEQ ID NO 4
<211> LENGTH: 1560
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 4

```
gtcgacgccg ccaccatgaa gtgcctgctg tacctggcct tcctgagcat cggcgtgaac      60
tgcaagttca ccatcgtgtt ccccccacaac cagaagggca cctggaagaa cgtgcccagc    120
aactaccact actgccccag cagcagcgat ctgaactggc acaacgacct gatcggcacc    180
gccctgcagg tgaagatgcc caagagccac aaggccatcc aggccgacgg ctggatgtgc    240
cacgccagca gtgggtgac cacctgcgac ttcagatggt acggccccaa gtacatcacc      300
cacagcatca ggagcttcac ccctagcgtg gagcagtgca gggagagcat cgagcagacc    360
aagcagggca catggctgaa tcctggcttc cctccccaga gctgcggcta cgccaccgtg    420
accgacgccg aggccgtgat cgtgcaggtg accccccacc acgtgctggt cgatgagtac    480
accggcgagt gggtggacag ccagttcatc aacggcaagt gcagcaacga catctgcccc    540
accgtgcaca acagcaccac ctggcacagc gactacaaag tgaagggcct gtgcgacagc    600
aacctgatca gcatggacat caccttttc agcgaggacg cgcgagctgag cagcctgggc    660 aaggagggca ccggcttcag aagcaaccac ttcgcctacg agaccggcga caaggcctgc    720
aagatgcagt actgcaagca ctggggagtg agactgccca gcggcgtgtg gttcgagatg    780
gccgaccagg acctgttcgc cgccgccaga ttccccgagt gccccgaggg cagcagcatc    840
agcgccccca gccagaccag cgtggatgtg agcctgatcc aggacgtgga gcggatcctg    900
gattacagcc tgtgccagga gacctggagc aagatcggag ccggcctgcc catcagcccc    960
gtggacctga gctacctggc ccctaagaac cccggcaccg gcccagcctt caccatcatc   1020
aacgggaccc tgaagtactt cgagacccgg tacatcagag tggacattgc cgcccctatc   1080
ctgagcagaa tggtgggcat gatcagcggc accaccaccg agagagagct gtgggacgat   1140 tgggccccctt acgaggatgt ggagatcggc cctaacggcg tgctgagaac cagcagcggc   1200
tacaagttcc ccctgtacat gatcggccac ggcatgctgg acagcgacct gcacctgagc   1260
agcaaggccc aggtgttcga gcaccccac atccaggacg ccgccagcca gctgcccgac   1320
gacgagaccc tgttcttcgg cgacaccggc ctgagcaaga accctatcga actggtggag   1380
ggctggttca gcggctggaa gagcagcatc gccagctttt tcttcatcat cggcctgatc   1440
atcgggctgt ttctggtgct gagagtgggc atctacctgt gcatcaagct gaagcacacc   1500
aagaagcggc aaatctacac cgacatcgag atgaaccggc tgggcaagtg atgaagatct   1560
```

<210> SEQ ID NO 5

```
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcagcatcgc cagcttcttc ttcatcatcg gcc                                  33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggccgatgat gaagaagaag ctggcgatgc tgc                                  33

<210> SEQ ID NO 7
<211> LENGTH: 1536
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
atgaagtgcc tgctgtacct ggccttcctg agcatcggcg tgaactgcaa gttcaccatc     60
gtgttccccc acaaccagaa gggcacctgg aagaacgtgc ccagcaacta ccactactgc    120
cccagcagca gcgatctgaa ctggcacaac gacctgatcg caccgccct gcaggtgaag     180 atgcccaaga gccacaaggc catccaggcc gacggctgga tgtgccacgc cagcaagtgg    240
gtgaccacct gcgacttcag atggtacggc cccaagtaca tcacccacag catcaggagc    300 ttcacccta gcgtggagca gtgcagggag agcatcgagc agaccaagca gggcacatgg    360
ctgaatcctg gcttccctcc ccagagctgc ggctacgcca ccgtgaccga cgccgaggcc    420
gtgatcgtgc aggtgacccc ccaccacgtg ctggtcgatg agtacaccgg cgagtgggtg    480
gacagccagt tcatcaacgg caagtgcagc aacgacatct gccccaccgt gcacaacagc    540
accacctggc acagcgacta caaagtgaag ggcctgtgcg acagcaacct gatcagcatg    600
gacatcacct ttttcagcga ggacggcgag ctgagcagcc tgggcaagga gggcaccggc    660
ttcagaagca accacttcgc ctacgagacc ggcgacaagg cctgcaagat gcagtactgc    720
aagcactggg gagtgagact gcccagcggc gtgtggttcg agatggccga ccaggacctg    780
ttcgccgccg ccagattccc cgagtgcccc gagggcagca gcatcagcgc ccccagccag    840
accagcgtgg atgtgagcct gatccaggac gtggagcgga tcctggatta cagcctgtgc    900
caggagacct ggagcaagat cggagccggc ctgcccatca gccccgtgga cctgagctac    960 ctggcccta agaaccccgg caccggccca gccttcacca tcatcaacgg gaccctgaag   1020
tacttcgaga cccggtacat cagagtggac attgccgccc ctatcctgag cagaatggtg   1080
ggcatgatca gcggcaccac caccgagaga gagctgtggg acgattgggc cccttacgag   1140
gatgtggaga tcgccctaa cggcgtgctg agaaccagca gcggctacaa gttccccctg   1200
tacatgatcg gcacggcat gctggacagc gacctgcacc tgagcagcaa ggcccaggtg   1260
ttcgagcacc cccacatcca ggacgccgcc agccagctgc ccgacgacga gaccctgttc   1320
ttcggcgaca ccggcctgag caagaaccct atcgaactgg tggagggctg gttcagcggc   1380
```

```
tggaagagca gcatcgccag cttcttcttc atcatcggcc tgatcatcgg gctgtttctg    1440
gtgctgagag tgggcatcta cctgtgcatc aagctgaagc acaccaagaa gcggcaaatc    1500
tacaccgaca tcgagatgaa ccggctgggc aagtga                              1536
```

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
cgcgatatcc gttaagtttg tatcgtaatg aagtgcctgc tgtacctggc ct              52
```

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
ctagactcga gctatcatca cttgcccagc cggttcat                              38
```

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
cccacatcat caccgtgac                                                   19
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
tcctagggat cacagggctc t                                                21
```

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
cgcgatatcc gttaagtttg tatcgtaatg aagtgcctgc tgtacctggc ct              52
```

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctgctggtt ctcagcacgc cgtt                                          24

<210> SEQ ID NO 14
<211> LENGTH: 3829
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1807)..(3357)

<400> SEQUENCE: 14
tcacacagga aacagctatg accatgatta cgaattgcgg ccgcaattct gaatgttaaa    60
tgttatactt tggatgaagc tataaatatg cattggaaaa ataatccatt taagaaagg   120 attcaaatac tacaaaacct aagcgataat atgttaacta agcttattct taacgacgct   180
ttaaatatac acaaataaac ataattttg tataacctaa caaataacta aacataaaa    240 ataataaaag gaaatgtaat atcgtaatta ttttactcag gaatgggtt aaatatttat   300 atcacgtgta tatctatact gttatcgtat actctttaca attactatta cgaatatgca   360
agagataata agattacgta tttaagagaa tcttgtcatg ataattgggt acgacatagt   420
gataaatgct atttcgcatc gttacataaa gtcagttgga agatggatt tgacagatgt    480 aacttaatag gtgcaaaaat gttaaataac agcattctat cggaagatag gataccagtt   540
atattataca aaaatcactg gttggataaa acagattctg caatattcgt aaaagatgaa   600
gattactgcg aatttgtaaa ctatgacaat aaaaagccat ttatctcaac gacatcgtgt   660
aattcttcca tgttttatgt atgtgtttca gatattatga gattactata aactttttgt   720
atacttatat tccgtaaact atattaatca tgaagaaaat gaaaaagtat agaagctgtt   780
cacgagcggt tgttgaaaac aacaaaatta tacattcaag atggcttaca tatacgtctg   840
tgaggctatc atggataatg acaatgcatc tctaaatagg tttttggaca atggattcga   900
ccctaacacg gaatatggta ctctacaatc tcctcttgaa atggctgtaa tgttcaagaa   960
taccgaggct ataaaaatct tgatgaggta tggagctaaa cctgtagtta ctgaatgcac  1020
aacttcttgt ctgcatgatg cggtgttgag agacgactac aaaatagtga agatctgtt   1080 gaagaataac tatgtaaaca atgttcttta cagcggaggc tttactcctt tgtgtttggc  1140
agcttacctt aacaaagtta atttggttaa acttctattg gctcattcgg cggatgtaga  1200
tatttcaaac acggatcggt taactcctct acatatagcc gtatcaaata aaaatttaac  1260
aatggttaaa cttctattga acaaaggtgc tgatactgac ttgctggata acatgggacg  1320
tactccttta atgatcgctg tacaatctgg aaatattgaa atatgtagca cactacttaa  1380
aaaaaataaa atgtccagaa ctgggaaaaa ttgatcttgc cagctgtaat tcatggtaga  1440
aaagaagtgc tcaggctact tttcaacaaa ggagcagatg taaactacat ctttgaaaga  1500
aatgaaaaat catatactgt tttggaattg attaaagaaa gttactctga cacacaaaag  1560
aggtagctga gtggtactc tcaaaggtac gtgactaatt agctataaaa aggatccggg  1620
ttaattaatt agtcatcagg cagggcgaga acgagactat ctgctcgtta attaattaga  1680
gcttctttat tctatactta aaaagtgaaa ataaatacaa aggttcttga gggttgtgtt  1740
aaattgaaag cgagaaataa tcataaatta tttcattatc gcgatatccg ttaagtttgt  1800 atcgta atg ctg tcc tac ctg atc ctg gcc atc atc gtg tcc cct atc     1848

```
            Met Leu Ser Tyr Leu Ile Leu Ala Ile Ile Val Ser Pro Ile
              1               5                  10 ctg ggc aag atc gag atc gtg ttc ccc cag cac acc acc ggc gat tgg    1896
Leu Gly Lys Ile Glu Ile Val Phe Pro Gln His Thr Thr Gly Asp Trp
 15              20                  25                  30 aag aga gtg ccc cac gag tac aac tac tgc cct acc agc gcc gac aag    1944
Lys Arg Val Pro His Glu Tyr Asn Tyr Cys Pro Thr Ser Ala Asp Lys
                 35                  40                  45 aat agc cac ggc acc cag acc ggc atc ccc gtg gag ctg acc atg ccc    1992
Asn Ser His Gly Thr Gln Thr Gly Ile Pro Val Glu Leu Thr Met Pro
             50                  55                  60 aag ggc ctg acc acc cac cag gtg gac ggc ttc atg tgc cac agc gcc    2040
Lys Gly Leu Thr Thr His Gln Val Asp Gly Phe Met Cys His Ser Ala
             65                  70                  75 ctg tgg atg acc acc tgt gac ttc aga tgg tac ggc ccc aag tac atc    2088
Leu Trp Met Thr Thr Cys Asp Phe Arg Trp Tyr Gly Pro Lys Tyr Ile
         80                  85                  90 acc cac agc atc cac aac gag gag ccc acc gat tac cag tgc ctg gag    2136
Thr His Ser Ile His Asn Glu Glu Pro Thr Asp Tyr Gln Cys Leu Glu
 95                 100                 105                 110 gcc atc aag gcc tac aag gac gga gtg ggc ttc aat cct ggc ttc ccc    2184
Ala Ile Lys Ala Tyr Lys Asp Gly Val Gly Phe Asn Pro Gly Phe Pro
                115                 120                 125 ccc cag agc tgt ggc tac ggc acc gtg acc gac gcc gag gcc cac atc    2232
Pro Gln Ser Cys Gly Tyr Gly Thr Val Thr Asp Ala Glu Ala His Ile
            130                 135                 140 atc acc gtg acc ccc cac agc gtg aag gtg gac gag tac acc ggc gag    2280
Ile Thr Val Thr Pro His Ser Val Lys Val Asp Glu Tyr Thr Gly Glu
            145                 150                 155 tgg atc gac ccc cac ttc atc ggc ggc agg tgt aag ggc aaa atc tgt    2328
Trp Ile Asp Pro His Phe Ile Gly Gly Arg Cys Lys Gly Lys Ile Cys
160                 165                 170 gag acc gtg cac aac agc acc aag tgg ttc acc agc agc gac ggc gag    2376
Glu Thr Val His Asn Ser Thr Lys Trp Phe Thr Ser Ser Asp Gly Glu
175                 180                 185                 190 agc gtg tgt agc cag ctg ttc acc ctg gtg ggc ggc acc ttc ttc agc    2424
Ser Val Cys Ser Gln Leu Phe Thr Leu Val Gly Gly Thr Phe Phe Ser
                195                 200                 205 gac agc gag gag atc acc agc atg ggc ctg ccc gag aca ggc atc cgg    2472
Asp Ser Glu Glu Ile Thr Ser Met Gly Leu Pro Glu Thr Gly Ile Arg
            210                 215                 220 agc aac tac ttc ccc tac atc agc acc gag ggc atc tgt aag atg cca    2520
Ser Asn Tyr Phe Pro Tyr Ile Ser Thr Glu Gly Ile Cys Lys Met Pro
            225                 230                 235 ttt tgc cgg aag cct ggc tac aag ctg aag aac gac ctg tgg ttc cag    2568
Phe Cys Arg Lys Pro Gly Tyr Lys Leu Lys Asn Asp Leu Trp Phe Gln
240                 245                 250 atc acc gac ccc gac ctg gac aag aca gtg aga gac ctg ccc cac atc    2616
Ile Thr Asp Pro Asp Leu Asp Lys Thr Val Arg Asp Leu Pro His Ile
255                 260                 265                 270 aag gac tgt gac ctg agc agc agc atc atc acc cct ggc gag cac gcc    2664
Lys Asp Cys Asp Leu Ser Ser Ser Ile Ile Thr Pro Gly Glu His Ala
                275                 280                 285 acc gat atc agc ctg atc agc gac gtg gag cgg atc ctg gac tac gcc    2712
Thr Asp Ile Ser Leu Ile Ser Asp Val Glu Arg Ile Leu Asp Tyr Ala
            290                 295                 300 ctg tgc cag aat acc tgg ggg aag atc gag gcc ggc gag ccc atc acc    2760
Leu Cys Gln Asn Thr Trp Gly Lys Ile Glu Ala Gly Glu Pro Ile Thr
            305                 310                 315 ccc gtg gac ctg agc tac ctg ggc cct aag aat ccc gga gtg ggc cct    2808
```

```
Pro Val Asp Leu Ser Tyr Leu Gly Pro Lys Asn Pro Gly Val Gly Pro
    320                 325                 330 gtg ttc acc atc atc aac agc agc ctg cac tac ttc acc agc aag tac    2856
Val Phe Thr Ile Ile Asn Ser Ser Leu His Tyr Phe Thr Ser Lys Tyr
335                 340                 345                 350 ctg agg gtg gag ctg gag agc cct gtg atc cct agg atg gag ggc aga    2904
Leu Arg Val Glu Leu Glu Ser Pro Val Ile Pro Arg Met Glu Gly Arg
                355                 360                 365 gtg gcc ggc acc agg att gtg aga cag ctg tgg gac cag tgg ttc ccc    2952
Val Ala Gly Thr Arg Ile Val Arg Gln Leu Trp Asp Gln Trp Phe Pro
            370                 375                 380 ttc ggc gag gcc gag atc ggc ccc aac ggc gtg ctg aaa acc aag cag    3000
Phe Gly Glu Ala Glu Ile Gly Pro Asn Gly Val Leu Lys Thr Lys Gln
        385                 390                 395 ggc tac aag ttc ccc ctg cac atc atc ggc aca ggc gag gtg gac agc    3048
Gly Tyr Lys Phe Pro Leu His Ile Ile Gly Thr Gly Glu Val Asp Ser
    400                 405                 410 gac atc aag atg gag agg atc gtg aag cac tgg gag cac cct cac atc    3096
Asp Ile Lys Met Glu Arg Ile Val Lys His Trp Glu His Pro His Ile
415                 420                 425                 430 gag gcc gcc cag acc tac ctg aag aag gac gac acc gag gag gtg atc    3144
Glu Ala Ala Gln Thr Tyr Leu Lys Lys Asp Asp Thr Glu Glu Val Ile
                435                 440                 445 tac tac ggc gac acc ggc atc agc aag aac cct gtg gaa ctg gtg gag    3192
Tyr Tyr Gly Asp Thr Gly Ile Ser Lys Asn Pro Val Glu Leu Val Glu
            450                 455                 460 ggc tgg ttc agc ggc tgg agg agc agc att atg ggc gtg gtg gcc gtg    3240
Gly Trp Phe Ser Gly Trp Arg Ser Ser Ile Met Gly Val Val Ala Val
        465                 470                 475 atc atc ggc ttc gtg atc ctg atc ttc ctg atc cgg ctg atc ggc gtg    3288
Ile Ile Gly Phe Val Ile Leu Ile Phe Leu Ile Arg Leu Ile Gly Val
    480                 485                 490 ctg tcc agc ctg ttc cgg cct aag cgg agg cct atc tac aag tcc gac    3336
Leu Ser Ser Leu Phe Arg Pro Lys Arg Arg Pro Ile Tyr Lys Ser Asp
495                 500                 505                 510 gtg gag atg gcc cac ttc cgg tgatgatttt tatgactagt taatcacggc       3387
Val Glu Met Ala His Phe Arg
                515 cgcttataaa gatctaaaat gcataatttc taaataatga aaaaaagtac atcatgagca  3447 acgcgttagt atattttaca atggagatta acgctctata ccgttctatg tttattgatt  3507 cagatgatgt tttagaaaag aaagttattg aatatgaaaa ctttaatgaa gatgaagatg  3567 acgacgatga ttattgttgt aaatctgttt tagatgaaga agatgacgcg ctaaagtata  3627 ctatggttac aaagtataag tctatactac taatggcgac ttgtgcaaga aggtatagta  3687 tagtgaaaat gttgttagat tatgattatg aaaaaccaaa taaatcagat ccatatctaa  3747 aggtatctcc tttgcacata atttcatcta ttcctagttt agaatacctg cagccaagct  3807 tggcactggc cgtcgtttta ca                                          3829

<210> SEQ ID NO 15
<211> LENGTH: 517
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 15

Met Leu Ser Tyr Leu Ile Leu Ala Ile Ile Val Ser Pro Ile Leu Gly
1               5                   10                  15
```

```
Lys Ile Glu Ile Val Phe Pro Gln His Thr Thr Gly Asp Trp Lys Arg
             20                  25                  30

Val Pro His Glu Tyr Asn Tyr Cys Pro Thr Ser Ala Asp Lys Asn Ser
         35                  40                  45

His Gly Thr Gln Thr Gly Ile Pro Val Glu Leu Thr Met Pro Lys Gly
     50                  55                  60

Leu Thr Thr His Gln Val Asp Gly Phe Met Cys His Ser Ala Leu Trp
 65                  70                  75                  80

Met Thr Thr Cys Asp Phe Arg Trp Tyr Gly Pro Lys Tyr Ile Thr His
             85                  90                  95

Ser Ile His Asn Glu Glu Pro Thr Asp Tyr Gln Cys Leu Glu Ala Ile
             100                 105                 110

Lys Ala Tyr Lys Asp Gly Val Gly Phe Asn Pro Gly Phe Pro Pro Gln
             115                 120                 125

Ser Cys Gly Tyr Gly Thr Val Thr Asp Ala Glu Ala His Ile Ile Thr
             130                 135                 140

Val Thr Pro His Ser Val Lys Val Asp Glu Tyr Thr Gly Glu Trp Ile
145                 150                 155                 160

Asp Pro His Phe Ile Gly Gly Arg Cys Lys Gly Lys Ile Cys Glu Thr
                165                 170                 175

Val His Asn Ser Thr Lys Trp Phe Thr Ser Ser Asp Gly Glu Ser Val
             180                 185                 190

Cys Ser Gln Leu Phe Thr Leu Val Gly Gly Thr Phe Phe Ser Asp Ser
             195                 200                 205

Glu Glu Ile Thr Ser Met Gly Leu Pro Glu Thr Gly Ile Arg Ser Asn
             210                 215                 220

Tyr Phe Pro Tyr Ile Ser Thr Glu Gly Ile Cys Lys Met Pro Phe Cys
225                 230                 235                 240

Arg Lys Pro Gly Tyr Lys Leu Lys Asn Asp Leu Trp Phe Gln Ile Thr
                245                 250                 255

Asp Pro Asp Leu Asp Lys Thr Val Arg Asp Leu Pro His Ile Lys Asp
             260                 265                 270

Cys Asp Leu Ser Ser Ile Ile Thr Pro Gly His Ala Thr Asp
             275                 280                 285

Ile Ser Leu Ile Ser Asp Val Glu Arg Ile Leu Asp Tyr Ala Leu Cys
             290                 295                 300

Gln Asn Thr Trp Gly Lys Ile Glu Ala Gly Glu Pro Ile Thr Pro Val
305                 310                 315                 320

Asp Leu Ser Tyr Leu Gly Pro Lys Asn Pro Gly Val Gly Pro Val Phe
                325                 330                 335

Thr Ile Ile Asn Ser Ser Leu His Tyr Phe Thr Ser Lys Tyr Leu Arg
             340                 345                 350

Val Glu Leu Glu Ser Pro Val Ile Pro Arg Met Glu Gly Arg Val Ala
             355                 360                 365

Gly Thr Arg Ile Val Arg Gln Leu Trp Asp Gln Trp Phe Pro Phe Gly
     370                 375                 380

Glu Ala Glu Ile Gly Pro Asn Gly Val Leu Lys Thr Lys Gln Gly Tyr
385                 390                 395                 400

Lys Phe Pro Leu His Ile Ile Gly Thr Gly Glu Val Asp Ser Asp Ile
                405                 410                 415

Lys Met Glu Arg Ile Val Lys His Trp Glu His Pro His Ile Glu Ala
             420                 425                 430

Ala Gln Thr Tyr Leu Lys Lys Asp Asp Thr Glu Glu Val Ile Tyr Tyr
```

435                 440                 445
Gly Asp Thr Gly Ile Ser Lys Asn Pro Val Glu Leu Val Glu Gly Trp
    450                 455                 460

Phe Ser Gly Trp Arg Ser Ser Ile Met Gly Val Val Ala Val Ile Ile
465                 470                 475                 480

Gly Phe Val Ile Leu Ile Phe Leu Ile Arg Leu Ile Gly Val Leu Ser
                485                 490                 495

Ser Leu Phe Arg Pro Lys Arg Arg Pro Ile Tyr Lys Ser Asp Val Glu
            500                 505                 510

Met Ala His Phe Arg
        515

<210> SEQ ID NO 16
<211> LENGTH: 3840
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1800)..(3332)

<400> SEQUENCE: 16
ggaaacagct atgaccatga ttacgaattg cggccgcaat tctgaatgtt aaatgttata      60
ctttggatga agctataaat atgcattgga aaataatcc atttaaagaa aggattcaaa      120
tactacaaaa cctaagcgat aatatgttaa ctaagcttat tcttaacgac gctttaaata    180
tacacaaata aacataattt ttgtataacc taacaaataa ctaaaacata aaaataataa    240
aaggaaatgt aatatcgtaa ttattttact caggaatggg gttaaatatt tatatcacgt    300
gtatatctat actgttatcg tatactcttt acaattacta ttacgaatat gcaagagata    360
ataagattac gtatttaaga gaatcttgtc atgataattg ggtacgacat agtgataaat    420
gctatttcgc atcgttacat aaagtcagtt ggaaagatgg atttgacaga tgtaacttaa    480
taggtgcaaa aatgttaaat aacagcattc tatcggaaga taggatacca gttatattat    540
acaaaaatca ctggttggat aaaacagatt ctgcaatatt cgtaaaagat gaagattact    600
gcgaatttgt aaactatgac aataaaaagc catttatctc aacgacatcg tgtaattctt    660
ccatgtttta tgtatgtgtt tcagatatta tgagattact ataaactttt tgtatactta    720
tattccgtaa actatattaa tcatgaagaa atgaaaaag tatagaagct gttcacgagc    780
ggttgttgaa acaacaaaa ttatacattc aagatggctt acatatacgt ctgtgaggct    840
atcatggata atgacaatgc atctctaaat aggttttgg acaatggatt cgaccctaac    900
acggaatatg gtactctaca atctcctctt gaaatggctg taatgttcaa gaataccgag    960
gctataaaaa tcttgatgag gtatggagct aaacctgtag ttactgaatg cacaacttct    1020
tgtctgcatg atgcggtgtt gagagacgac tacaaaatag tgaaagatct gttgaagaat    1080
aactatgtaa acaatgttct ttacagcgga ggctttactc ctttgtgttt ggcagcttac    1140
cttaacaaag ttaatttggt taaacttcta ttggctcatt cggcggatgt agatatttca    1200
aacacggatc ggttaactcc tctacatata gccgtatcaa ataaaatttt aacaatggtt    1260
aaacttctat tgaacaaagg tgctgatact gacttgctgg ataacatggg acgtactcct    1320
ttaatgatcg ctgtacaatc tggaaatatt gaaatatgta gcacactact taaaaaaat    1380 aaaatgtcca gaactgggaa aaattgatct tgccagctgt aattcatggt agaaaagaag    1440
tgctcaggct acttttcaac aaaggagcag atgtaaacta catctttgaa agaaatggaa    1500

```
aatcatatac tgttttggaa ttgattaaag aaagttactc tgagcacaa  aagaggtagc   1560 tgaagtggta ctctcaaagg tacgtgacta attagctata aaaaggatcc gggttaatta   1620
attagtcatc aggcagggcg agaacgagac tatctgctcg ttaattaatt agagcttctt   1680
tattctatac ttaaaaagtg aaaataaata caaaggttct tgagggttgt gttaaattga   1740
aagcgagaaa taatcataaa ttatttcatt atcgcgatat ccgttaagtt tgtatcgta    1799
```

| | | | | | | | | | | | | | | | | |
|---|---|---|---|---|---|---|---|---|---|---|---|---|---|---|---|---|
| atg | aag | tgc | ctg | ctg | tac | ctg | gcc | ttc | ctg | agc | atc | ggc | gtg | aac | tgc | 1847 |
| Met | Lys | Cys | Leu | Leu | Tyr | Leu | Ala | Phe | Leu | Ser | Ile | Gly | Val | Asn | Cys | |
| 1 | | | | 5 | | | | | 10 | | | | | 15 | | |

| aag | ttc | acc | atc | gtg | ttc | ccc | cac | aac | cag | aag | ggc | acc | tgg | aag | aac | 1895 |
|---|---|---|---|---|---|---|---|---|---|---|---|---|---|---|---|---|
| Lys | Phe | Thr | Ile | Val | Phe | Pro | His | Asn | Gln | Lys | Gly | Thr | Trp | Lys | Asn | |
| | | | 20 | | | | | 25 | | | | | 30 | | | |

| gtg | ccc | agc | aac | tac | cac | tac | tgc | ccc | agc | agc | agc | gat | ctg | aac | tgg | 1943 |
|---|---|---|---|---|---|---|---|---|---|---|---|---|---|---|---|---|
| Val | Pro | Ser | Asn | Tyr | His | Tyr | Cys | Pro | Ser | Ser | Ser | Asp | Leu | Asn | Trp | |
| | | | 35 | | | | | 40 | | | | | 45 | | | |

| cac | aac | gac | ctg | atc | ggc | acc | gcc | ctg | cag | gtg | aag | atg | ccc | aag | agc | 1991 |
|---|---|---|---|---|---|---|---|---|---|---|---|---|---|---|---|---|
| His | Asn | Asp | Leu | Ile | Gly | Thr | Ala | Leu | Gln | Val | Lys | Met | Pro | Lys | Ser | |
| 50 | | | | | 55 | | | | | 60 | | | | | | |

| cac | aag | gcc | atc | cag | gcc | gac | ggc | tgg | atg | tgc | cac | gcc | agc | aag | tgg | 2039 |
|---|---|---|---|---|---|---|---|---|---|---|---|---|---|---|---|---|
| His | Lys | Ala | Ile | Gln | Ala | Asp | Gly | Trp | Met | Cys | His | Ala | Ser | Lys | Trp | |
| 65 | | | | | 70 | | | | | 75 | | | | | 80 | |

| gtg | acc | acc | tgc | gac | ttc | aga | tgg | tac | ggc | ccc | aag | tac | atc | acc | cac | 2087 |
|---|---|---|---|---|---|---|---|---|---|---|---|---|---|---|---|---|
| Val | Thr | Thr | Cys | Asp | Phe | Arg | Trp | Tyr | Gly | Pro | Lys | Tyr | Ile | Thr | His | |
| | | | | 85 | | | | | 90 | | | | | 95 | | |

| agc | atc | agg | agc | ttc | acc | cct | agc | gtg | gag | cag | tgc | agg | gag | agc | atc | 2135 |
|---|---|---|---|---|---|---|---|---|---|---|---|---|---|---|---|---|
| Ser | Ile | Arg | Ser | Phe | Thr | Pro | Ser | Val | Glu | Gln | Cys | Arg | Glu | Ser | Ile | |
| | | | 100 | | | | | 105 | | | | | 110 | | | |

| gag | cag | acc | aag | cag | ggc | aca | tgg | ctg | aat | cct | ggc | ttc | cct | ccc | cag | 2183 |
|---|---|---|---|---|---|---|---|---|---|---|---|---|---|---|---|---|
| Glu | Gln | Thr | Lys | Gln | Gly | Thr | Trp | Leu | Asn | Pro | Gly | Phe | Pro | Pro | Gln | |
| | | | 115 | | | | | 120 | | | | | 125 | | | |

| agc | tgc | ggc | tac | gcc | acc | gtg | acc | gac | gcc | gag | gcc | gtg | atc | gtg | cag | 2231 |
|---|---|---|---|---|---|---|---|---|---|---|---|---|---|---|---|---|
| Ser | Cys | Gly | Tyr | Ala | Thr | Val | Thr | Asp | Ala | Glu | Ala | Val | Ile | Val | Gln | |
| | | | 130 | | | | | 135 | | | | | 140 | | | |

| gtg | acc | ccc | cac | cac | gtg | ctg | gtc | gat | gag | tac | acc | ggc | gag | tgg | gtg | 2279 |
|---|---|---|---|---|---|---|---|---|---|---|---|---|---|---|---|---|
| Val | Thr | Pro | His | His | Val | Leu | Val | Asp | Glu | Tyr | Thr | Gly | Glu | Trp | Val | |
| 145 | | | | | 150 | | | | | 155 | | | | | 160 | |

| gac | agc | cag | ttc | atc | aac | ggc | aag | tgc | agc | aac | gac | atc | tgc | ccc | acc | 2327 |
|---|---|---|---|---|---|---|---|---|---|---|---|---|---|---|---|---|
| Asp | Ser | Gln | Phe | Ile | Asn | Gly | Lys | Cys | Ser | Asn | Asp | Ile | Cys | Pro | Thr | |
| | | | | 165 | | | | | 170 | | | | | 175 | | |

| gtg | cac | aac | agc | acc | acc | tgg | cac | agc | gac | tac | aaa | gtg | aag | ggc | ctg | 2375 |
|---|---|---|---|---|---|---|---|---|---|---|---|---|---|---|---|---|
| Val | His | Asn | Ser | Thr | Thr | Trp | His | Ser | Asp | Tyr | Lys | Val | Lys | Gly | Leu | |
| | | | 180 | | | | | 185 | | | | | 190 | | | |

| tgc | gac | agc | aac | ctg | atc | agc | atg | gac | atc | acc | ttt | ttc | agc | gag | gac | 2423 |
|---|---|---|---|---|---|---|---|---|---|---|---|---|---|---|---|---|
| Cys | Asp | Ser | Asn | Leu | Ile | Ser | Met | Asp | Ile | Thr | Phe | Phe | Ser | Glu | Asp | |
| | | | 195 | | | | | 200 | | | | | 205 | | | |

| ggc | gag | ctg | agc | agc | ctg | ggc | aag | gag | ggc | acc | ggc | ttc | aga | agc | aac | 2471 |
|---|---|---|---|---|---|---|---|---|---|---|---|---|---|---|---|---|
| Gly | Glu | Leu | Ser | Ser | Leu | Gly | Lys | Glu | Gly | Thr | Gly | Phe | Arg | Ser | Asn | |
| | | | 210 | | | | | 215 | | | | | 220 | | | |

| cac | ttc | gcc | tac | gag | acc | ggc | gac | aag | gcc | tgc | aag | atg | cag | tac | tgc | 2519 |
|---|---|---|---|---|---|---|---|---|---|---|---|---|---|---|---|---|
| His | Phe | Ala | Tyr | Glu | Thr | Gly | Asp | Lys | Ala | Cys | Lys | Met | Gln | Tyr | Cys | |
| 225 | | | | | 230 | | | | | 235 | | | | | 240 | |

| aag | cac | tgg | gga | gtg | aga | ctg | ccc | agc | ggc | gtg | tgg | ttc | gag | atg | gcc | 2567 |
|---|---|---|---|---|---|---|---|---|---|---|---|---|---|---|---|---|
| Lys | His | Trp | Gly | Val | Arg | Leu | Pro | Ser | Gly | Val | Trp | Phe | Glu | Met | Ala | |
| | | | | 245 | | | | | 250 | | | | | 255 | | |

| gac | cag | gac | ctg | ttc | gcc | gcc | gcc | aga | ttc | ccc | gag | tgc | ccc | gag | ggc | 2615 |
|---|---|---|---|---|---|---|---|---|---|---|---|---|---|---|---|---|
| Asp | Gln | Asp | Leu | Phe | Ala | Ala | Ala | Arg | Phe | Pro | Glu | Cys | Pro | Glu | Gly | |
| | | | 260 | | | | | 265 | | | | | 270 | | | |

| agc | agc | atc | agc | gcc | ccc | agc | cag | acc | agc | gtg | gat | gtg | agc | ctg | atc | 2663 |

|  |  |  |  |  |  |  |  |  |  |  |  |  |
|---|---|---|---|---|---|---|---|---|---|---|---|---|
| Ser | Ser | Ile | Ser | Ala | Pro | Ser | Gln | Thr | Ser | Val | Asp | Val | Ser | Leu | Ile |
|  |  | 275 |  |  |  | 280 |  |  |  | 285 |  |  |

```
cag gac gtg gag cgg atc ctg gat tac agc ctg tgc cag gag acc tgg    2711
Gln Asp Val Glu Arg Ile Leu Asp Tyr Ser Leu Cys Gln Glu Thr Trp
    290             295                 300 agc aag atc gga gcc ggc ctg ccc atc agc ccc gtg gac ctg agc tac    2759
Ser Lys Ile Gly Ala Gly Leu Pro Ile Ser Pro Val Asp Leu Ser Tyr
305             310                 315                 320 ctg gcc cct aag aac ccc ggc acc ggc cca gcc ttc acc atc atc aac    2807
Leu Ala Pro Lys Asn Pro Gly Thr Gly Pro Ala Phe Thr Ile Ile Asn
                325                 330                 335 ggg acc ctg aag tac ttc gag acc cgg tac atc aga gtg gac att gcc    2855
Gly Thr Leu Lys Tyr Phe Glu Thr Arg Tyr Ile Arg Val Asp Ile Ala
            340                 345                 350 gcc cct atc ctg agc aga atg gtg ggc atg atc agc ggc acc acc acc    2903
Ala Pro Ile Leu Ser Arg Met Val Gly Met Ile Ser Gly Thr Thr Thr
        355                 360                 365 gag aga gag ctg tgg gac gat tgg gcc cct tac gag gat gtg gag atc    2951
Glu Arg Glu Leu Trp Asp Asp Trp Ala Pro Tyr Glu Asp Val Glu Ile
370                 375                 380 ggc cct aac ggc gtg ctg aga acc agc agc ggc tac aag ttc ccc ctg    2999
Gly Pro Asn Gly Val Leu Arg Thr Ser Ser Gly Tyr Lys Phe Pro Leu
385                 390                 395                 400 tac atg atc ggc cac ggc atg ctg gac agc gac ctg cac ctg agc agc    3047
Tyr Met Ile Gly His Gly Met Leu Asp Ser Asp Leu His Leu Ser Ser
                405                 410                 415 aag gcc cag gtg ttc gag cac ccc cac atc cag gac gcc gcc agc cag    3095
Lys Ala Gln Val Phe Glu His Pro His Ile Gln Asp Ala Ala Ser Gln
            420                 425                 430 ctg ccc gac gac gag acc ctg ttc ttc ggc gac acc ggc ctg agc aag    3143
Leu Pro Asp Asp Glu Thr Leu Phe Phe Gly Asp Thr Gly Leu Ser Lys
        435                 440                 445 aac cct atc gaa ctg gtg gag ggc tgg ttc agc ggc tgg aag agc agc    3191
Asn Pro Ile Glu Leu Val Glu Gly Trp Phe Ser Gly Trp Lys Ser Ser
450                 455                 460 atc gcc agc ttc ttc ttc atc atc ggc ctg atc atc ggg ctg ttt ctg    3239
Ile Ala Ser Phe Phe Phe Ile Ile Gly Leu Ile Ile Gly Leu Phe Leu
                465                 470                 475                 480 gtg ctg aga gtg ggc atc tac ctg tgc atc aag ctg aag cac acc aag    3287
Val Leu Arg Val Gly Ile Tyr Leu Cys Ile Lys Leu Lys His Thr Lys
            485                 490                 495 aag cgg caa atc tac acc gac atc gag atg aac cgg ctg ggc aag        3332
Lys Arg Gln Ile Tyr Thr Asp Ile Glu Met Asn Arg Leu Gly Lys
        500                 505                 510 tgatgatagc tcgagtctag aatcgatccc gggttttat gactagttaa tcacggccgc    3392
ttataaagat ctaaaatgca taatttctaa ataatgaaaa aaagtacatc atgagcaacg    3452
cgttagtata ttttacaatg gagattaacg ctctataccg ttctatgttt attgattcag    3512
atgatgtttt agaaaagaaa gttattgaat atgaaaactt taatgaagat gaagatgacg    3572
acgatgatta ttgttgtaaa tctgttttag atgaagaaga tgacgcgcta agtatacta    3632 tggttacaaa gtataagtct atactactaa tggcgacttg tgcaagaagg tatagtatag    3692
tgaaaatgtt gttagattat gattatgaaa aaccaaataa atcagatcca tatctaaagg    3752
tatctccttt gcacataatt tcatctattc ctagtttaga ataccatgcag ccaagcttgg    3812 cactggccgt cgttttacaa cgtcgtga                                      3840
```

<210> SEQ ID NO 17
<211> LENGTH: 511

<212> TYPE: PRT
<213> ORGANISM: Artificial Sequence
<220> FEATURE:
<223> OTHER INFORMATION: Description of Artificial Sequence: Synthetic construct

<400> SEQUENCE: 17

```
Met Lys Cys Leu Leu Tyr Leu Ala Phe Leu Ser Ile Gly Val Asn Cys
 1               5                  10                  15

Lys Phe Thr Ile Val Phe Pro His Asn Gln Lys Gly Thr Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Arg Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

His Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Gln Asp Leu Phe Ala Ala Arg Phe Pro Glu Cys Pro Glu Gly
            260                 265                 270

Ser Ser Ile Ser Ala Pro Ser Gln Thr Ser Val Asp Val Ser Leu Ile
    275                 280                 285

Gln Asp Val Glu Arg Ile Leu Asp Tyr Ser Leu Cys Gln Glu Thr Trp
    290                 295                 300

Ser Lys Ile Gly Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380
```

-continued

```
Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Thr Leu Phe Phe Gly Asp Thr Gly Leu Ser Lys
        435                 440                 445

Asn Pro Ile Glu Leu Val Glu Gly Trp Phe Ser Gly Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile Tyr Leu Cys Ile Lys Leu Lys His Thr Lys
                485                 490                 495

Lys Arg Gln Ile Tyr Thr Asp Ile Glu Met Asn Arg Leu Gly Lys
            500                 505                 510
```